United States Patent
Selaru et al.

(10) Patent No.: US 11,149,275 B2
(45) Date of Patent: Oct. 19, 2021

(54) DEVICE AND METHOD TO TREAT ESOPHAGEAL DISORDERS

(71) Applicant: THE JOHNS HOPKINS UNIVERSITY, Baltimore, MD (US)

(72) Inventors: Florin M. Selaru, Catonsville, MD (US); Stephen J. Meltzer, Lutherville, MD (US); George L. Coles, Baltimore, MD (US); Honggang Cui, Lutherville, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/727,653

(22) Filed: Oct. 9, 2017

(65) Prior Publication Data
US 2018/0179543 A1    Jun. 28, 2018

Related U.S. Application Data

(60) Provisional application No. 62/406,164, filed on Oct. 10, 2016.

(51) Int. Cl.

| | | |
|---|---|---|
| *A61K 48/00* | (2006.01) | |
| *C07H 21/02* | (2006.01) | |
| *C12N 15/113* | (2010.01) | |
| *A61P 35/00* | (2006.01) | |
| *A61K 47/46* | (2006.01) | |
| *A61K 9/00* | (2006.01) | |
| *A61K 9/48* | (2006.01) | |
| *A61K 47/42* | (2017.01) | |
| *A61K 9/70* | (2006.01) | |
| *A61K 9/50* | (2006.01) | |
| *A61K 9/06* | (2006.01) | |

(52) U.S. Cl.
CPC ........ *C12N 15/1135* (2013.01); *A61K 9/0053* (2013.01); *A61K 9/4808* (2013.01); *A61K 47/46* (2013.01); *A61P 35/00* (2018.01); *C12N 15/113* (2013.01); *A61K 9/0065* (2013.01); *A61K 9/06* (2013.01); *A61K 9/5068* (2013.01); *A61K 9/70* (2013.01); *A61K 47/42* (2013.01); *C12N 2310/141* (2013.01); *C12N 2320/32* (2013.01)

(58) Field of Classification Search
CPC ... C12N 15/111; C12N 15/115; C12N 15/113; C12N 2310/141
See application file for complete search history.

(56) References Cited

U.S. PATENT DOCUMENTS

| | | |
|---|---|---|
| 5,399,363 A | 3/1995 | Liversidge et al. |
| 5,466,468 A | 11/1995 | Schneider et al. |
| 5,543,158 A | 8/1996 | Gref et al. |
| 5,580,579 A | 12/1996 | Ruddy et al. |
| 5,629,001 A | 5/1997 | Michael et al. |
| 5,641,515 A | 6/1997 | Ramtoola |
| 5,725,871 A | 3/1998 | Illum |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 6,613,308 B2 | 9/2003 | Bartus et al. |
| 8,679,759 B2 | 3/2014 | Selaru et al. |
| 2016/0331686 A1* | 11/2016 | Polach .................. A61K 9/127 |

FOREIGN PATENT DOCUMENTS

| | | | |
|---|---|---|---|
| CA | 2812650 A1 | 4/2012 | |
| WO | 2007045896 A1 | 4/2007 | |
| WO | WO 2011/057003 A2 * | 5/2011 | ........... C12N 15/113 |
| WO | 2012135091 A2 | 10/2012 | |
| WO | 2015156964 A1 | 10/2015 | |

OTHER PUBLICATIONS

Hu et al. (Biomacromolecules, 2009, 10(4), 756-765).*
Roh et al. (ACS Nano, vol. 8, No. 10, 2014, 9767-9780).*
Bertrand et al. (Biochemical and Biophysical Research Communications, 296, 2002, 1000-1004).*
Wickremasinghe et al. (Biomacromolecules, 2014, 15, 3587-3595).*
Wu et al. (Cancer Prev Res, 2013, 6(3) 196-205).*
Hazzah et al., International Journal of Pharmaceutics, 492, 2015, 248-257.*
Takenaga, M., et al., "Microparticle resins as a potential nasal drug delivery system for insulin" Journal of Controlled Release 52 (1998) 81-87.
Kulcheski, F., "Circular RNAs are miRNA sponges and can be used as a new class of biomarker" Journal of Biotechnology 238 (2016) 42-51.
Maley, et al., Selectively advantageous mutations and hitchhikers in neoplasms: p16 lesions are selected in Barrett's esophagus. Cancer Res. 2004;64(10):3414-27.
Dawsey, et al., Squamous dysplasia and early esophageal cancer in the Linxian region of China: distinctive endoscopic lesions. Gastroenterology. 1993;105(5):1333-40.
Galipeau, et al., 17p (p53) allelic losses, 4N (G2/tetraploid) populations, and progression to aneuploidy in Barrett's esophagus. Proc Natl Acad Sci. 1996;93(14):7081-4.
Halm, et al., Apoptosis and cell proliferation in the metaplasia-dysplasia-carcinoma-sequence of Barrett's esophagus. Hepatogastroenterology. 2000;47(34):962-6.
Reid, et al., Predictors of progression to cancer in Barrett's esophagus: baseline histology and flow cytometry identify low- and high-risk patient subsets. Am J Gastroenterol. 2000;95(7):1669-76.
Rabinovitch, et al., Predictors of progression in Barrett's esophagus III: baseline flow cytometric variables. Am J Gastroenterol. 2001;96(11):3071-83.

(Continued)

*Primary Examiner* — Amy H Bowman
(74) *Attorney, Agent, or Firm* — Casimir Jones, S.C.; Melissa Karabinis

(57) ABSTRACT

Described are devices for treating disease in subjects wherein the devices include a sponge comprising a hydrogel, extracellular vesicles (EVs), and an agent. Methods of using the devices to treat or prevent disease such as esophageal adenocarcinoma are also described.

14 Claims, 9 Drawing Sheets

Specification includes a Sequence Listing.

(56) References Cited

OTHER PUBLICATIONS

Maley, et al., The combination of genetic instability and clonal expansion predicts progression to esophageal adenocarcinoma. Cancer Res. 2004;64(20):7629-33.
Feber, et al., MicroRNA expression profiles of esophageal cancer. J Thorac Cardiovasc Surg. 2008;135(2):255-60; discussion 60.
Maru, et al., MicroRNA-196a is a potential marker of progression during Barrett's metaplasia-dysplasia-invasive adenocarcinoma sequence in esophagus. Am J Pathol. 2009;174(5):1940-8.
Mathe, et al., MicroRNA expression in squamous cell carcinoma and adenocarcinoma of the esophagus: associations with survival. Clin Cancer Res. 2009;15(19):6192-200.
Yang, et al., MicroRNA expression signatures in Barrett's esophagus and esophageal adenocarcinoma. Clin Cancer Res. 2009;15(18):5744-52.
Bansal, et al., Discovery and validation of Barrett's esophagus microRNA transcriptome by next generation sequencing. PLoS One. 2013;8(1):e54240.
Derecka, et al., Transient exposure to low levels of insecticide affects metabolic networks of honeybee larvae. PLoS One. 2013;8(7):e68191.
Fassan, et al., The HER2-miR125a5p/miR125b loop in gastric and esophageal carcinogenesis. Hum Pathol. 2013;44(9):1804-10.
Garman, et al., MicroRNA expression differentiates squamous epithelium from Barrett's esophagus and esophageal cancer. Dig Dis Sci. 2013;58(11):3178-88.
Matsuzaki, et al., Bile acids increase levels of microRNAs 221 and 222, leading to degradation of CDX2 during esophageal carcinogenesis. Gastroenterology. 2013;145(6):1300-11.
Revilla-Nuin, et al., Predictive value of MicroRNAs in the progression of barrett esophagus to adenocarcinoma in a long-term follow-up study. Ann Surg. 2013;257(5):886-93.
Russo, et al., The molecular changes driving the carcinogenesis in Barrett's esophagus: which came first, the chicken or the egg? Critical reviews in oncology/hematology. 2013;86(3):278-89.
Saad, et al., Deciphering the unique microRNA signature in human esophageal adenocarcinoma. PLoS One. 2013;8(5):e64463.
Sakai, et al., A review of the current understanding and clinical utility of miRNAs in esophageal cancer. Semin Cancer Biol. 2013;23(6 Pt B):512-21.
Streppel, et al., MicroRNA 223 is upregulated in the multistep progression of Barrett's esophagus and modulates sensitivity to chemotherapy by targeting PARP1. Clin Cancer Res. 2013;19(15):4067-78.
Van Baal, et al., microRNA-145 in Barrett's oesophagus: regulating BMP4 signalling via GATA6. Gut. 2013;62(5):664-75.
Wu, et al., MicroRNA expression signatures during malignant progression from Barrett's esophagus to esophageal adenocarcinoma. Cancer Prev Res (Phila). 2013;6(3):196-205.
Bus, et al., Upregulation of miRNA-143, -145, -192, and -194 in esophageal epithelial cells upon acidic bile salt stimulation. Dis Esophagus. 2014;27(6):591-600.
Chiam, et al., Circulating Serum Exosomal miRNAs As Potential Biomarkers for Esophageal Adenocarcinoma. J Gastrointest Surg. 2015;19(7):1208-15.
Steele, et al., Clinical potential of microRNAs in pancreatic ductal adenocarcinoma. Pancreas. 2011. 40(8):1165-71.
Amodio, et al., miR-29s: a family of epi-miRNAs with therapeutic implications in hematologic malignancies. Oncotarget. 2015;6(15):12837-61.
Fang, et al., MicroRNAs targeting prostate cancer stem cells. Experimental biology and medicine. Aug. 2015; 240(8):1071-1078.
Kaboli, et al., MicroRNA-based therapy and breast cancer: A comprehensive review of novel therapeutic strategies from diagnosis to treatment. Pharmacological research : the official journal of the Italian Pharmacological Society. 2015;97:104-21.
Liu, et al., Role of microRNAs in hepatocellular carcinoma. Frontiers in bioscience. 2015;20:1056-67.
Naidu, et al., MiRNA-based therapeutic intervention of cancer. Journal of hematology & oncology. 2015;8(1):68.
Perry, et al., Role of microRNAs in allergic asthma: present and future. Current opinion in allergy and clinical immunology. 2015;15(2):156-62.
Reddy, MicroRNA (miRNA) in cancer. Cancer cell international. 2015;15:38.
Shi, et al., Mechanisms and therapeutic potential of microRNAs in hypertension. Drug discovery today. Oct. 2015; 20(10): 1188-1204.
Alexander, et al., Exosome-delivered microRNAs modulate the inflammatory response to endotoxin. Nature communications. 2015;6:7321.
O'Driscoll, Expanding on exosomes and ectosomes in cancer. N Engl J Med. 2015;372(24):2359-62.
Matsumura, et al., Exosomal microRNA in serum is a novel biomarker of recurrence in human colorectal cancer. Br J Cancer. Jul. 14, 2015;113(2):275-81.
Challagundla, et al., Exosome-Mediated Transfer of microRNAs Within the Tumor Microenvironment and Neuroblastoma Resistance to Chemotherapy. J Natl Cancer Inst. 2015;107(7).
Haug, et al., Exosome-like Extracellular Vesicles from MYCN-amplified Neuroblastoma Cells Contain Oncogenic miRNAs. Anticancer Res. 2015;35(5):2521-30.
Das, et al., Extracellular vesicle microRNA transfer in cardiovascular disease. Cardiovascular pathology : the official journal of the Society for Cardiovascular Pathology. 2015;24(4):199-206.
Hannon, et al., The expanding universe of noncoding RNAs. Cold Spring Harbor symposia on quantitative biology. 2006;71:551-64.
Ghildiyal, et al., Small silencing RNAs: an expanding universe. Nat Rev Genet. 2009;10(2):94-108.
Haybaeck, et al., The parallel universe: microRNAs and their role in chronic hepatitis, liver tissue damage and hepatocarcinogenesis. Swiss medical weekly. 2011;141:w13287.
Xue, et al., An expanding universe of the non-coding genome in cancer biology. Carcinogenesis. 2014;35(6):1209-16.
Shu, Cytopathology of the esophagus. An overview of esophageal cytopathology in China. Acta Cytol. 1983;27(1):7-16.
Greenebaum, et al., Use of the esophageal balloon in the diagnosis of carcinomas of the head, neck and upper gastrointestinal tract. Acta Cytol. 1984;28(1):9-15.
Lightdale, et al., Screening diagnosis and staging of esophageal cancer. Semin Oncol. 1984;11(2):101 -12.
Korsten, et al., Balloon cytology in screening of asymptomatic alcoholics for esophageal cancer, Part I. Dig Dis Sci. 1985;30(9):845-51.
Tsang, et al., Reliability of balloon-mesh cytology in detecting esophageal carcinoma in a population of US veterans. Cancer. 1987;59(3):556-9.
Lucas, Argument for esophageal cancer screening in high risk U.S. populations. The Journal of the Florida Medical Association. 1990;77(5):526-9.
Wahl, et al., Molecular hybridization of immobilized nucleic acids: theoretical concepts and practical considerations. Methods Enzymol. 1987;152:399-407.
Kimmel, et al., Identification and characterization of specific clones: strategy for confirming the validity of presumptive clones. Methods Enzymol. 1987;152:507-11.
Sato, et al., Long-term expansion of epithelial organoids from human colon, adenoma, adenocarcinoma, and Barrett's epithelium. Gastroenterology. 2011;141(5):1762-72.
Bader, et al., Developing therapeutic microRNAs for cancer. Gene Ther. 2011.18(12):1121-6.
Chen, et al., Nanoparticles modified with tumor-targeting scFv deliver siRNA and miRNA for cancer therapy. Mol Ther. 2010. 18(9):1650-6.
Garzon, et al., Targeting microRNAs in cancer: rationale, strategies and challenges. Nat Rev Drug Discov. 2010. 9(10):775-89.
Kota, et al., Therapeutic microRNA delivery suppresses tumorigenesis in a murine liver cancer model. Cell. 2009;137(6):1005-17.
Wang, et al., Potential uses of microRNA in lung cancer diagnosis, prognosis, and therapy. Curr Cancer Drug Targets. 2009;9(4):572-94.

(56) References Cited

OTHER PUBLICATIONS

Li, et al., uman bile contains microRNA-laden extracellular vesicles that can be used for cholangiocarcinoma diagnosis. Hepatology. Sep. 2014;60(3):896-907.
Li, et al., Refinement of a bile-based extracellular vesicle-derived MicroRNA panel. Hepatology. Sep. 2014 ; 60(3): 896-907.
Hvid-Jensen, et al., Incidence of adenocarcinoma among patients with Barrett's esophagus. N Engl J Med. 2011;365(15):1375-83.
Spechler, et al., Barrett's esophagus. The New England journal of medicine. 2014;371(9):836-45.
Skacel, et al., The diagnosis of low-grade dysplasia in Barrett's esophagus and its implications for disease progression. Am J Gastroenterol. 2000;95(12):3383-7.
Montgomery, et al., Dysplasia as a predictive marker for invasive carcinoma in Barrett esophagus: a follow-up study based on 138 cases from a diagnostic variability study. Hum Pathol. 2001;32(4):379-88.
Odze, Diagnosis and grading of dysplasia in Barrett's oesophagus. J Clin Pathol. 2006;59(10):1029-38.
Wani, et al., Low-grade dysplasia in Barrett's esophagus—an innocent bystander? Pro. Endoscopy. 2007;39(7):643-6.
Bhat, et al., Risk of malignant progression in Barrett's esophagus patients: results from a large population-based study. J Natl Cancer Inst. 2011;103(13):1049-57.
Sikkema, et al., Predictors for neoplastic progression in patients with Barrett's Esophagus: a prospective cohort study. Am J Gastroenterol. 2011;106(7):1231-8.
Spechler, Barrett esophagus and risk of esophageal cancer: a clinical review. JAMA. 2013;310(6):627-36.
Galipeau, et al., NSAIDs modulate CDKN2A, TP53, and DNA content risk for progression to esophageal adenocarcinoma. PLoS Med. 2007;4(2):e67.
Nguyen, et al., Medication usage and the risk of neoplasia in patients with Barrett's esophagus. Clin Gastroenterol Hepatol. 2009;7(12):1299-304.
Winberg, et al., Risk factors and chemoprevention in Barrett's esophagus—an update. Scand J Gastroenterol. 2012;47(4):397-406.
Morgan, et al., Barrett's oesophagus, oesophageal cancer and colon cancer: an explanation of the association and cancer chemopreventive potential of non-steroidal anti-inflammatory drugs. Eur J Cancer Prev. 1998;7(3):195-9.
Morris, et al., Cyclooxygenase-2 expression in the Barrett's metaplasia-dysplasia-adenocarcinoma sequence. Am J Gastroenterol. 2001;96(4):990-6.
Buskens, et al., Role of cyclooxygenase-2 in the development and treatment of oesophageal adenocarcinoma. Scandinavian journal of gastroenterology Supplement. 2003(239):87-93.
Hur, et al., Cost-effectiveness of aspirin chemoprevention for Barrett's esophagus. J Natl Cancer Inst. 2004;96(4):316-25.
Vaughan, et al., Non-steroidal anti-inflammatory drugs and risk of neoplastic progression in Barrett's oesophagus: a prospective study. Lancet Oncol. 2005;6(12):945-52.
Lagergren, Etiology and risk factors for oesophageal adenocarcinoma: possibilities for chemoprophylaxis? Best practice & research Clinical gastroenterology. 2006;20(5):803-12.
Heath, et al., Secondary chemoprevention of Barrett's esophagus with celecoxib: results of a randomized trial. J Natl Cancer Inst. 2007;99(7):545-57.
Jankowski, Aspirin chemoprevention in barrett esophagus: is the risk worth the benefit? Gastroenterology & hepatology. 2012;8(12):831-3.
Omer, et al., Aspirin protects against Barrett's esophagus in a multivariate logistic regression analysis. Clin Gastroenterol Hepatol. 2012;10(7):722-7.
Choi, et al., Statins and aspirin for chemoprevention in Barrett's esophagus: results of a cost-effectiveness analysis. Cancer Prev Res (Phila). 2014;7(3):341-50.
Zhang, et al., Cyclooxygenase inhibitors use is associated with reduced risk of esophageal adenocarcinoma in patients with Barrett's esophagus: a meta-analysis. Br J Cancer. 2014;110(9):2378-88.
Schneider, et al., Aspirin and nonsteroidal anti-inflammatory drug use and the risk of Barrett's esophagus. Dig Dis Sci. 2015;60(2):436-43.
Tsibouris, et al., Daily use of non-steroidal anti-inflammatory drugs is less frequent in patients with Barrett's oesophagus who develop an oesophageal adenocarcinoma. Alimentary pharmacology & therapeutics. 2004;20(6):645-55.
Thiagarajan, et al., Aspirin and NSAIDs; benefits and harms for the gut. Best practice & research Clinical gastroenterology. 2012;26(2):197-206.
Peura, et al., Aspirin and proton pump inhibitor combination therapy for prevention of cardiovascular disease and Barrett's esophagus. Postgraduate medicine. 2014;126(1):87-96.
Reid, et al., Barrett's esophagus. Correlation between flow cytometry and histology in detection of patients at risk for adenocarcinoma. Gastroenterology. 1987;93(1):1-11.
Levine, et al., Correlation of ultrastructural aberrations with dysplasia and flow cytometric abnormalities in Barrett's epithelium. Gastroenterology. 1989;96(2 Pt 1):355-67.
Rabinovitch, et al., Progression to cancer in Barrett's esophagus is associated with genomic instability. Lab Invest. 1989;60(1):65-71.
Reid, et al., Flow-cytometric and histological progression to malignancy in Barrett's esophagus: prospective endoscopic surveillance of a cohort. Gastroenterology. 1992;102(4 Pt 1):1212-9.
Blount, et al., 17p allelic losses in diploid cells of patients with Barrett's esophagus who develop aneuploidy. Cancer Res. 1994;54(9):2292-5.
Meltzer, et al., Reduction to homozygosity involving p53 in esophageal cancers demonstrated by the polymerase chain reaction. Proc Natl Acad Sci U S A. 1991;88(11):4976-80.
Boynton, et al., Frequent loss of heterozygosity at the retinoblastoma locus in human esophageal cancers. Cancer Res. 1991;51(20):5766-9.
Boynton, et al., . Loss of heterozygosity involving the APC and MCC genetic loci occurs in the majority of human esophageal cancers. Proc Natl Acad Sci U S A. 1992;89(8):3385-8.
Huang, et al., Loss of heterozygosity involves multiple tumor suppressor genes in human esophageal cancers. Cancer Res. 1992;52(23):6525-30.
Tarmin, et al., Frequent loss of heterozygosity on chromosome 9 in adenocarcinoma and squamous cell carcinoma of the esophagus. Cancer Res. 1994;54(23):6094-6.
Blount, et al., 17p allelic deletions and p53 protein overexpression in Barrett's adenocarcinoma. Cancer Res. 1991;51(20):5482-6.
Blount, et al., Clonal ordering of 17p and 5q allelic losses in Barrett dysplasia and adenocarcinoma. Proc Natl Acad Sci U S A. 1993;90(8):3221-5.
Zhou, et al., The MTS1 gene is frequently mutated in primary human esophageal tumors. Oncogene. 1994;9(12):3737-41.
Koss, Cytologic diagnosis of oral, esophageal, and peripheral lung cancer. Journal of cellular biochemistry Supplement. 1993;17F:66-81.
Shen, et al., Cytologic screening for esophageal cancer: results from 12,877 subjects from a high-risk population in China. Int J Cancer. 1993;54(2):185-8.
Dawsey, et al., Esophageal cytology and subsequent risk of esophageal cancer. A prospective follow-up study from Linxian, China. Acta Cytol. 1994;38(2):183-92.
Liu, et al., Esophageal balloon cytology and subsequent risk of esophageal and gastric-cardia cancer in a high-risk Chinese population. Int J Cancer. 1994;57(6):775-80.
Gerson, et al., Screening for esophageal adenocarcinoma: an evidence-based approach. Am J Med. 2002;113(6):499-505.
Yang, et al., Cytologic screening for esophageal cancer in a high-risk population in Anyang County, China. Acta Cytol. 2002;46(3):445-52.
Wang, et al., Cytological screening and 15 years' follow-up (1986-2001) for early esophageal squamous cell carcinoma and precan-

(56) References Cited

OTHER PUBLICATIONS cerous lesions in a high-risk population in Anyang County, Henan Province, Northern China. Cancer detection and prevention. 2005;29(4):317-22.
Lao-Sireix, et al., Non-endoscopic screening biomarkers for Barrett's oesophagus: from microarray analysis to the clinic. Gut. 2009;58(11):1451-9.
Kadri, et al., Acceptability and accuracy of a non-endoscopic screening test for Barrett's oesophagus in primary care: cohort study. BMJ. 2010;341:c4372.
Cui, et al., Self-assembly of peptide amphiphiles: from molecules to nanostructures to biomaterials. Biopolymers. 2010;94(1):1-18.
Cui, et al., Self-assembly of giant peptide nanobelts. Nano letters. 2009;9(3):945-51.
Cui, et al., Amino acid sequence in constitutionally isomeric tetrapeptide amphiphiles dictates architecture of one-dimensional nanostructures. Journal of the American Chemical Society. 2014;136(35):12461-8.
Lin, et al., Supramolecular nanostructures as drug carriers. Current Opinion in Chemical Engineering. 2015;7:75-83.
Aida, et al., Functional supramolecular polymers. Science. 2012;335(6070):813-7.
Gultepe, et al., Biologic tissue sampling with untethered microgrippers. Gastroenterology. 2013;144(4):691-3.
Gultepe, et al., Biopsy with thermally-responsive untethered microtools. Adv Mater. 2013;25(4):514-9.
Raposo, et al., Extracellular vesicles: exosomes, microvesicles, and friends. J Cell Biol. 2013;200(4):373-83.
Sirica, et al., A novel "patient-like" model of cholangiocarcinoma progression based on bile duct inoculation of tumorigenic rat cholangiocyte cell lines. Hepatology. 2008;47(4):1178-90.
Dubois, et al., Nonsteroidal anti-inflammatory drugs, eicosanoids, and colorectal cancer prevention. Gastroenterol Clin North Am. 1996;25(4):773-91.
Chiu, et al., Sulindac causes rapid regression of preexisting tumors in Min/+ mice independent of prostaglandin biosynthesis. Cancer Res. 1997;57(19):4267-73.
Richard, et al., Sulindac for periampullary polyps in FAP patients. International journal of colorectal disease. 1997;12(1):14-8.
Chen, et al., Aberrant arachidonic acid metabolism in esophageal adenocarcinogenesis, and the effects of sulindac, nordihydroguaiaretic acid, and alpha-difluoromethylornithine on tumorigenesis in a rat surgical model. Carcinogenesis. 2002;23(12):2095-102.
Scheper, et al., Sulindac induces apoptosis and inhibits tumor growth in vivo in head and neck squamous cell carcinoma. Neoplasia. 2007;9(3):192-9.
Buttar, et al., Chemoprevention of esophageal adenocarcinoma by COX-2 inhibitors in an animal model of Barrett's esophagus Gastroenterology. 2002;122(4):1101-12.
Timme, et al., STAT3 expression, activity and functional consequences of STAT3 inhibition in esophageal squamous cell carcinomas and Barrett's adenocarcinomas. Oncogene. 2014;33(25):3256-66.
Zhang, et al., Cancer-related inflammation and Barrett's carcinogenesis: interleukin-6 and STAT3 mediate apoptotic resistance in transformed Barrett's cells. Am J Physiol Gastrointest Liver Physiol. 2011;300(3):G454-60.
Dvorak, et al., Role of interleukin-6 in Barrett's esophagus pathogenesis. World J Gastroenterol. 2013;19(15):2307-12.
Yu, et al., Mitochondrial STAT3 Contributes to Transformation of Barrett's Epithelial Cells that Express Oncogenic Ras in a p53-Independent Fashion. Am J Physiol Gastrointest Liver Physiol. 2015:ajpgi 00462 2014.
Nikitakis, et al., The nonsteroidal anti-inflammatory drug sulindac causes down-regulation of signal transducer and activator of transcription 3 in human oral squamous cell carcinoma cells. Cancer Res. 2002;62(4):1004-7.
Merino, et al., Nanocomposite Hydrogels: 3D Polymer-Nanoparticle Synergies for On-Demand Drug Delivery. ACS nano. 2015;9(5):4686-97.
Baek, et al., In Situ Assembly of Anti-Fouling/Bacterial Silver Nanoparticle-Hydrogel Composites with Controlled Particle Release and Matrix Softening. ACS applied materials & interfaces. 2015, 7 (28), pp. 15359-15367.
Zhang, et al., Self-assembled Tat nanofibers as effective drug carrier and transporter. ACS nano. 2013;7(7):5965-77.
Lin, et al., Multiwalled nanotubes formed by catanionic mixtures of drug amphiphiles. ACS nano. 2014;8(12):12690-700.
Cheetham, et al., Supramolecular nanostructures formed by anticancer drug assembly. Journal of the American Chemical Society. 2013;135(8):2907-10.
Tusher, et al., Significance analysis of microarrays applied to the ionizing radiation response. Proc Natl Acad Sci U S A. 2001;98(9):5116-21.
Zhou, et al., Growth suppression of esophageal cancer cells by p16INK4 and p15INK4B in vitro. Cancer J Sci Am. 1996;2(4):221-4.
Esteller, et al., p14ARF silencing by promoter hypermethylation mediates abnormal intracellular localization of MDM2. Cancer Res. 2001;61(7):2816-21.
Agarwal, et al., Epigenomic program of Barrett's-associated neoplastic progression reveals possible involvement of insulin signaling pathways. Endocr Relat Cancer. 2012;19(1):L5-9.
Yang, et al., Long non-coding RNA HNF1A-AS1 regulates proliferation and migration in oesophageal adenocarcinoma cells. Gut. Jun. 2014;63(6):881-90.
Sato, et al., Resolution of liver cirrhosis using vitamin A-coupled liposomes to deliver siRNA against a collagen-specific chaperone. Nature biotechnology. 2008;26(4):431-42.
Yamanaka, et al., Coordinated effects of microRNA-494 induce G(2)/M arrest in human cholangiocarcinoma. Cell Cycle. 2012;11(14):2729-38.
Olaru, et al., A microRNA downregulated in human cholangiocarcinoma controls cell cycle through multiple targets involved in the G1/S checkpoint. Hepatology. Dec. 2011;54(6):2089-98.
Ito, et al., Involvement of TSLC1 in progression of esophageal squamous cell carcinoma. Cancer Res. 2003;63(19):6320-6.
Newcomb, et al., Cell death versus cell survival instructed by supramolecular cohesion of nanostructures. Nature communications. 2014;5:3321.
Frederix, et al., Exploring the sequence space for (tri-)peptide self-assembly to design and discover new hydrogels. Nature chemistry. 2015;7(1):30-7.
Ambros, The functions of animal microRNAs. Nature. Sep. 16, 2004;431(7006):350-5.
Lee, et al., The C. elegans heterochronic gene lin-4 encodes small RNAs with antisense complementarity to lin-14. Cell. Dec. 3, 1993;75(5):843-54.
Wang, et al., Updated guidelines 2008 for the diagnosis, surveillance and therapy of Barrett's esophagus. Am J Gastroenterol. Mar. 2008;103(3):788-97.
Metzler, et al., High expression of precursor microRNA-155/BIC RNA in children with Burkitt lymphoma. Genes Chromosomes Cancer. Feb. 2004;39(2):167-9.
Hollstein, et al., Frequent mutation of the p53 gene in human esophageal cancer. Proc Natl Acad Sci U S A. 1990;87(24):9958-61.
Bennett, et al., p53 mutation and protein accumulation during multistage human esophageal carcinogenesis. Cancer Res. 1992;52(21):6092-7.
Lei, et al., Infrequent DPC4 gene mutation in esophageal cancer, gastric cancer and ulcerative colitis-associated neoplasms. Oncogene. 1996;13(11):2459-62.
Schneider, et al.,Mutations of p53 in Barrett's esophagus and Barrett's cancer: a prospective study of ninety-eight cases. J Thorac Cardiovasc Surg. 1996;111(2):323-31; discussion 31-3.
Muzeau, et al., Loss of heterozygosity on chromosome 9 and p16 (MTS1, CDKN2) gene mutations in esophageal cancers. Int J Cancer. 1997;72(1):27-30.
Casson, et al., p53 gene mutations in Barrett's epithelium and esophageal cancer. Cancer Res. 1991;51(16):4495-9.

(56) References Cited

OTHER PUBLICATIONS

Hollstein, et al., Genetic analysis of human esophageal tumors from two high incidence geographic areas: frequent p53 base substitutions and absence of ras mutations. Cancer Res. 1991;51(15):4102-6.

Sommerer, et al., Mutations of BRAF and KRAS2 in the development of Barrett's adenocarcinoma. Oncogene. 2004;23(2):554-8.

Phillips, et al., Mutation analysis of PIK3CA and PIK3CB in esophageal cancer and Barrett's esophagus. Int J Cancer. 2006;118(10):2644-6.

Paulson, et al., p16 mutation spectrum in the premalignant condition Barrett's esophagus. PLoS One. 2008;3(11):e3809.

Jin, et al., Hypermethylation of tachykinin-1 is a potential biomarker in human esophageal cancer. Clin Cancer Res. 2007;13(21):6293-300.

Orloff, et al., Germline mutations in MSR1, ASCC1, and CTHRC1 in patients with Barrett esophagus and esophageal adenocarcinoma. JAMA. 2011;306(4):410-9.

Hamilton, et al., Reprimo methylation is a potential biomarker of Barrett's-Associated esophageal neoplastic progression. Clin Cancer Res. 2006;12(22):6637-42.

Sato, et al., CpG island hypermethylation in progression of esophageal and gastric cancer. Cancer. 2006;106(3):483-93.

Schulmann, et al., Inactivation of p16, RUNX3, and HPP1 occurs early in Barrett's-associated neoplastic progression and predicts progression risk. Oncogene. 2005;24(25):4138-48. Epub Apr. 13, 2005. doi: 10.1038/sj.onc.1208598.

Jin, et al., Hypermethylation of the nel-like 1 gene is a common and early event and is associated with poor prognosis in early-stage esophageal adenocarcinoma. Oncogene. 2007;26(43):6332-40.

Jin, et al., Promoter hypermethylation of CDH13 is a common, early event in human esophageal adenocarcinogenesis and correlates with clinical risk factors. Int J Cancer. 2008;123(10):2331-6.

Jin, et al., Hypermethylation of the AKAP12 Promoter is a Biomarker of Barrett's-Associated Esophageal Neoplastic Progression. Cancer Epidemiol Biomarkers Prev. 2008;17(1):111-7.

Jin, et al., Hypermethylation of the somatostatin promoter is a common, early event in human esophageal carcinogenesis. Cancer. 2008;112(1):43-9.

Jin, et al., A multicenter, double-blinded validation study of methylation biomarkers for progression prediction in Barrett's esophagus. Cancer Res. 2009;69(10):4112-5.

Alvarez, et al., Widespread hypomethylation occurs early and synergizes with gene amplification during esophageal carcinogenesis. PLoS Genet. 2011;7(3):e1001356.

Jin, et al., MAL hypermethylation is a tissue-specific event that correlates with MAL mRNA expression in esophageal carcinoma. Scientific reports. 2013;3:2838.

Jin, et al., Endoglin promoter hypermethylation identifies a field defect in human primary esophageal cancer. Cancer. 2013;119(20):3604-9.

Wu, et al., Hypomethylation of Noncoding DNA Regions and Overexpression of the Long Noncoding Rna, AFAP1-AS1, in Barrett's Esophagus and Esophageal Adenocarcinoma. Gastroenterology. 2013;144:956-966.

Jin, et al., Temporal evolution in caveolin 1 methylation levels during human esophageal carcinogenesis. BMC Cancer. 2014;14:345.

Eads, et al., Fields of aberrant CpG island hypermethylation in Barrett's esophagus and associated adenocarcinoma. Cancer Res. 2000;60(18):5021-6.

Eads, et al., Epigenetic patterns in the progression of esophageal adenocarcinoma. Cancer Res. 2001;61(8):3410-8.

Meltzer, et al., Tissue-specific expression of c-Ha-ras in premalignant gastrointestinal mucosae. Exp Mol Pathol. 1989;51(3):264-74.

Huang, et al., Altered messenger RNA and unique mutational profiles of p53 and Rb in human esophageal carcinomas. Cancer Res. 1993;53(8):1889-94.

Huang, et al., A unique p53 intragenic deletion flanked by short direct repeats results in loss of mRNA expression in a human esophageal carcinoma. Carcinogenesis. 1994;15(8):1653-5.

Abraham, et al., Esophagin cDNA cloning and characterization: a tissue-specific member of the small proline-rich protein family that is not expressed in esophageal tumors. Cell Growth Differ. 1996;7(7):855-60.

Wilson, et al., Increased expression of inducible nitric oxide synthase and cyclooxygenase-2 in Barrett's esophagus and associated adenocarcinomas. Cancer Res. 1998;58(14):2929-34.

Sheikh, et al., The antiapoptotic decoy receptor TRID/TRAIL-R3 is a p53-regulated DNA damage-inducible gene that is overexpressed in primary tumors of the gastrointestinal tract. Oncogene. 1999;18(28):4153-9.

Selaru, et al., Global gene expression profiling in Barrett's esophagus and esophageal cancer: a comparative analysis using cDNA microarrays. Oncogene. 2002;21(3):475-8.

Xu, et al., Artificial neural networks and gene filtering distinguish between global gene expression profiles of Barrett's esophagus and esophageal cancer. Cancer Res. 2002;62(12):3493-7.

Brabender, et al., A multigene expression panel for the molecular diagnosis of Barrett's esophagus and Barrett's adenocarcinoma of the esophagus. Oncogene. 2004;23(27):4780-8.

Kimos, et al., Esophagin and proliferating cell nuclear antigen (PCNA) are biomarkers of human esophageal neoplastic progression. Int J Cancer. 2004;111(3):415-7.

Sato, et al., Polo-like kinase and survivin are esophageal tumor-specific promoters. Biochem Biophys Res Commun. 2006;342(2):465-71.

Wang, et al., Transcriptional profiling suggests that Barrett's metaplasia is an early intermediate stage in esophageal adenocarcinogenesis. Oncogene. 2006;25(23):3346-56.

Selaru, et al., Beyond Field Effect: Analysis of Shrunken Centroids in Normal Esophageal Epithelia Detects Concomitant Esophageal Adenocarcinoma. Bioinform Biol Insights. 2007;1:127-36.

Ito, et al., Polo-like kinase 1 regulates cell proliferation and is targeted by miR-593* in esophageal cancer. Int J Cancer. Nov. 1, 2011;129(9):2134-46.

Kan, et al., MicroRNAs in Barrett's esophagus and esophageal adenocarcinoma. Curr Opin Pharmacol. Dec. 2009; 9(6): 727-732.

Kan, et al., The miR-106b-25 polycistron, activated by genomic amplification, functions as an oncogene by suppressing p21 and Bim. Gastroenterology. 2009;136(5):1689-700.

David, et al., MicroRNA involvement in esophageal carcinogenesis. Curr Opin Pharmacol. Dec. 2011;11(6):612-6.

Galipeau, et al., Clonal expansion and loss of heterozygosity at chromosomes 9p and 17p in premalignant esophageal (Barrett's) tissue. J Natl Cancer Inst. 1999;91(24):2087-95.

Song, et al., MicroRNAs in pathogenesis, diagnosis, and treatment of gastroesophageal cancers. Gastroenterology. 2012;143(1):35-47 e2.

Raskind, et al., Persistent clonal areas and clonal expansion in Barrett's esophagus. Cancer Res. 1992;52(10):2946-50.

Reid, et al., Barrett's esophagus: cell cycle abnormalities in advancing stages of neoplastic progression. Gastroenterology. 1993;105(1):119-29.

Neshat, et al., Barrett's esophagus: a model of human neoplastic progression. Cold Spring Harbor symposia on quantitative biology. 1994;59:577-83.

Barret, et al., Evolution of neoplastic cell lineages in Barrett oesophagus. Nat Genet. 1999;22(1):106-9.

* cited by examiner

DEVICE AND METHOD TO TREAT ESOPHAGEAL DISORDERS

REFERENCE TO RELATED APPLICATIONS

This application claims the benefit of U.S. Provisional Patent Application No. 62/406,164 filed on Oct. 10, 2016, which is hereby incorporated by reference for all purposes as if fully set forth herein.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Oct. 2, 2017, is named P13713-02_SL.txt and is 925 bytes in size.

BACKGROUND OF THE INVENTION

Barrett's esophagus (BE) is a premalignant condition. Esophageal adenocarcinoma (EAC) risk in BE patients is increased 11-fold vs. the general population, and BE is considered the obligate precursor lesion of EAC. During BE-associated neoplastic evolution (BEAN), nondysplastic BE first progresses to low-grade dysplasia (LGD), then to high-grade dysplasia (HGD), and finally to EAC. LGD is a controversial pre-malignant lesion: estimates of relative neoplastic progression risk vs. nondysplastic BE range from 1.0 to 3.5. Nevertheless, LGD represents a turning point in the management: BE patients with LGD are customarily re-endoscoped at much shorter time intervals, typically every 3-6 months, until the LGD either spontaneously resolves or progresses. LGD exhibits a finite spontaneous regression rate, ranging from 30% to 80%; however, the long-term risk of BE patients with previously regressed LGD has not been determined. LGD patients are not deemed to have a sufficiently high risk to justify very invasive and complication-ridden esophagectomy but typically do not receive this treatment. They currently have no therapeutic options since there is no available relatively non-invasive, point-of-care therapeutic agent. LGD may progress to HGD, which is considered an extremely high-risk lesion, with chances of concomitant EAC elsewhere in the esophagus much greater than when HGD is not found; moreover, future progression rates to EAC range from 10% to 50% within 1 year of HGD diagnosis. Thus, HGD is usually treated with local removal, typically by endoscopic mucosal resection (EMR) of the HGD lesion, followed by radiofrequency (Barrx) ablation of all remaining BE mucosa, even nondysplastic BE. After EMR and Barrx, however, continued close (frequent) endoscopic surveillance is still required, since evidence does not support relaxing surveillance back to the customary 3-year interval for BE patients who never had HGD. Nonetheless, as of now, there are no relatively non-invasive therapeutic approaches for patients with HGD. These patients with HGD are not considered to be surgical/invasive therapeutic endoscopy candidates and cannot receive treatment. Thus, there is a pressing need for preventive interventions in BE patients with both LGD and HGD, and the current patent application is believed to provide the first non-invasive therapeutic options to these patients.

SUMMARY OF THE INVENTION

One embodiment of the present invention is a device for treating disease in a subject comprising a sponge wherein the sponge comprises a hydrogel, extracellular vesicles (EVs), and an agent. The agent maybe a small molecule chemical compound, antibody, nucleic acid molecule, or polypeptide, or fragments thereof but the preferred agent is a microRNA (miR). A suitable agent used in the present invention may have an anti-oncogenic effect in the presence of cancer cells, suppress one or more EAC pathways in the presence of EAC cells. Suitable microRNAs maybe be miRnA mimics, antagomirs, miR-25, miR-93, miR-106b, or a combination thereof and they may silence one or more of the tumor suppressor gene (TSG) in a cancer cell, such as p21, B-cell lymphoma 2 (BCL2)-L11, or a combination thereof. Many types of extracellular vesicles may be used in the present invention depending upon the application, such as fibroblast-derived extracellular vesicles. In addition, extracellular vesicles used in the present invention may be synthesized from a subject's own fibroblasts wherein the fibroblasts are cultured in vitro and the subject has a disease such as Barrett's esophagus (BE), as an example. Extracellular vesicles carrying the microRNA on the inside of the extracellular vesicles may be mixed, or incorporated with, one or more hydrogel and a sponge may be impregnated with the hydrogel comprising the extracellular vesicles. Many types of hydrogels may be used in the present invention depending upon the application such as a hydrogel comprising peptide nanofibers. There are many peptide nanofibers suitable for use in the present invention such as c16-HKD having the structure of formula I:

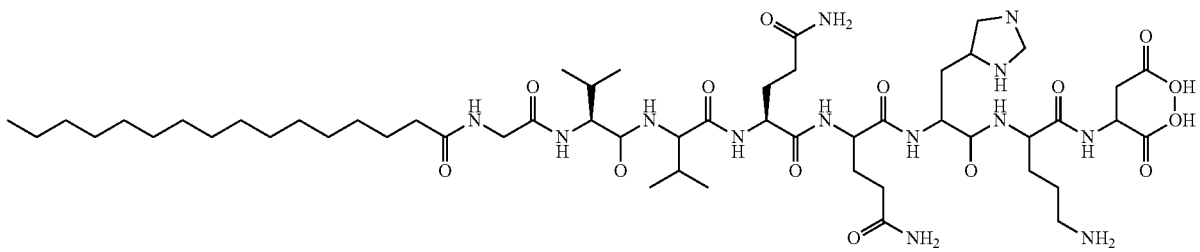 [SMILES: CCCCCCCCCCCCCCCC(=O)NCC(=O)N[C@@H](C(C)C)C(O)NC(C(=O)N[C@@H](CCC(N)=O)C(=O)NC(CCC(N)=O)C(=O)NC(CC1CNCN1)C(O)NC(CCCN)C(=O)NC1CC(=O)OOC1=O)C(C)C]

Many types of sponges may be used in the present invention depending upon the application and the sponge maybe tethered to a string, contain distance markings, and maybe capable of being swallowed by a subject, as examples. A device of the present invention may further comprise a capsule that dissolves after being swallowed wherein the sponge is located on the inside of the capsule.

Another embodiment of the present invention is a method of treating or preventing a disease in a subject comprising the steps of: having the subject swallow a device of the present invention; positioning the device so that it is located near diseased cells; transferring the agent from the sponge to the diseased cells; treating or preventing the disease in the subject such as a human. The method of the present invention may help subjects suffering from esophagus, low-grade dysplasia, high grade dysplasia, or esophageal adenocarcinoma, as examples. The methods of the present may treat the following types of diseased cells such as Barrett's esophagus cells, low-grade dysplasia cells, high grade dysplasia cells, esophageal adenocarcinoma cells, as examples. The methods of the present invention may be used by a subject, independently and without the help of a physician or medical assistant, to treat or prevent the subject's disease. Variations of the present invention include the sponge being squeezed by the lower esophageal sphincter releasing the extracellular vesicles, verify the transfer of extracellular vesicles and micoRNA by endoscopic biopsy, and using extracellular vesicles that are labelled, as examples.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function such as Indoleamine 2,3-dioxygenase (an oxidoreductase) catalyzing the degradation of the essential amino acid tryptophan (trp) to N-formyl-kynurenine.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "disease" is meant any condition or disorder that damages or interferes with the normal function of a cell, tissue, or organ. Examples of diseases include cancer.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "express" refers to the ability of a gene to express the gene product including for example its corresponding mRNA or protein sequence (s).

The term, "obtaining" as in "obtaining an agent" includes synthesizing, purchasing, or otherwise acquiring the agent.

By "modulator" refers to inducing or suppressing a gene or pathway, such as an EAC pathway.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" is meant a negative alteration of at least 10%, 25%, 50%, 75%, or 100%.

A "reference" or "control" refers to a standard or control conditions such as a sample (human cells) or a subject that is a free, or substantially free, of an agent such as one or more miRs of the present invention.

A "miR" or "microRNA" or "miRNA" is a small non-coding RNA molecule (containing about 22 nucleotides, for example) found in plants, animals and some viruses, that functions in RNA silencing and post-transcriptional regulation of gene expression. Examples of miRs used in the methods of the present invention include:

```
hsa-mir-106b MI0000734
                                   (SEQ ID NO: 1)
CCUGCCGGGGCUAAAGUGCUGACAGUGCAGAUAGUGGUCCUCUCCGUGC
UACCGCACUGUGGGUACUUGCUGCUCCAGCAGG Has-mir-93 MI0000095
                                   (SEQ ID NO: 2)
CUGGGGGCUCCAAAGUGCUGUUCGUGCAGGUAGUGUGAUUACCCAACCU
ACUGCUGAGCUAGCACUUCCCGAGCCCCGG hsa-mir-25 MI0000082
                                   (SEQ ID NO: 3)
GGCCAGUGUUGAGAGGCGGAGACUUGGGCAAUUGCUGGACGCUGCCCUG
GGCAUUGCACUUGUCUCGGUCUGACAGUGCCGGCC
```

As used herein, the term "sensitivity" is the percentage of subjects with a particular disease.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects).

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes one or more miRs of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes one or more miRs of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Such treatment (surgery and/or chemotherapy) will be suitably administered to subjects, particularly humans, suffering from, having, susceptible to, or at risk for cancer (such as EAC) or disease, disorder, or symptom thereof. Determination of those subjects "at risk" can be made by any objective or subjective determination by a diagnostic test or opinion of a subject or health care provider (e.g., genetic test, enzyme or protein marker, a marker (as defined herein), family history, and the like).

DETAILED DESCRIPTION OF THE INVENTION

Figure 1:
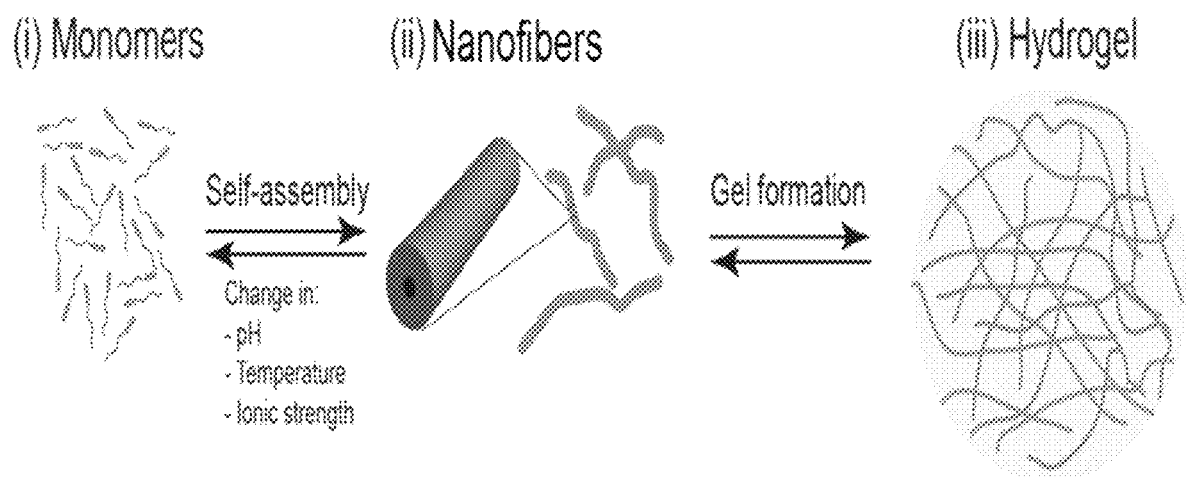
FIG. 1 illustrates the self-assembly of amphiphilic monomers into nanostructured supramolecular polymers that can then enmesh to form hydrogels. The process is reversible and tunable by various stimuli. The low viscosity of the monomeric state offers great flexibility in handling and processing. The resultant hydrogels can be used to directly carry hydrophilic EVs similar to other hydrogel systems made of hydrophilic covalent polymers.

Studies suggest BE undergoes a series of clonal evolutionary steps, characterized by clonal fields whose cells all contain an identical molecular abnormality. Such abnormalities include abnormal DNA content (aneuploidy), loss of heterozygosity (LOH), point mutation, altered methylation (both hyper- and hypo-), aberrant gene expression, and abnormal miR expression. It is widely believed that BEAN-causing molecular alterations arising within an already-established field lead to a growth advantage, with subsequent rapid expansion of a new field, often overgrowing or replacing its parent field. Eventually, histologic progression accompanies this molecular progression, until EAC occurs. BEAN-causing molecular alterations should still be present in the final tumor, since it arose from clonal fields containing these earlier alterations. The inventors of the present invention have early events could be countered some of these early events (specifically miR expression) to prevent later progression steps from occurring.

MicroRNAs in BEAN

Altered miR expression levels have been studied in BEAN occurring early and persisting late during progression. Interestingly, one recent report described circulating exosomal miRs as EAC biomarkers. The inventors have focused on miR alterations as attractive targets for manipulation for many reasons. Firstly, miRs (and mimics or antagomiRs derived from them) are extremely stable and robust, resisting degradation by nucleases present throughout the body. This robustness is even further amplified when miRs are enclosed within EVs, which also occurs naturally throughout the body. Thus, the inventors determined that leveraging miRs as therapeutic agents merely requires harnessing and manipulating physiological processes. Second, the inventors determined that the universe of miRs is conveniently small, consisting of only approximately 2,000 unique species, by comparison, the universe of genes comprises about 23,000 species, while the universe of mutations consists of hundreds of thousands of sequence alterations, and the protein universe contains millions of unique species. Thus, the inventors determined that it was much easier to comprehensively canvass the miR universe, and thereby were able to find the most suitable target miR species. Third, the inventors determined that miRs are uniquely powerful potential therapeutic agents, since each miR targets (and silences) somewhere between several dozen and several hundred different mRNAs. A miR can be thought of as a cluster bomb, each of whose individual bomblets will explode in a different place within the countryside of biochemical pathways and biological processes. Thus, the inventors determined that by repressing or inducing even a single miR would result in far-reaching phenotypic effects, resulting in profound alterations in cell or cancer biology.

The Therasponge©

Retrievable sponges and balloons have been studied as diagnostic devices for esophageal cancer. These devices have shown limited sensitivity in this context, largely due to the limitations of cytopathology in obtained specimens. More recently, the advent of molecular markers has substantially improved both the sensitivity and the specificity of these devices for the diagnosis of Barrett's esophagus. Nevertheless, to the best of the inventors' knowledge, no one has yet developed a sponge-based theranostic for distal esophageal diseases and the present invention is the first sponge-based theranostic for esophageal diseases.

Peptide-Based Supramolecular Nanofiber Hydrogels

In one embodiment, the inventors developed a sponge comprising a peptide-based supramolecular nanofiber hydrogels to assist with effective delivery of EVs to the esophagus. The inventors' strategy was to use rationally designed, small molecule peptide amphiphiles, as molecular building units to create functional supramolecular polymers and hydrogels. The basic design is illustrated in FIG. 1. Under carefully chosen conditions, these rationally designed monomers (FIG. 1.i.) can self-assemble into 1D nanofibers (FIG. 1.ii), which can further entangle and enmesh into supramolecular hydrogels (FIG. 1.iii). For supramolecular hydrogels, the gelation and monomeric states can be readily tuned by varying temperature or solution pH, while the extremely low viscosity of the monomeric state offers great flexibility for processing and handling (e.g., injectable materials). The inventors' determined the most intriguing properties that favor the use of peptide-based materials as drug carriers in the present application are their inherent biocompatibility and biodegradability. Importantly, the inventors' also determined that the degradation of peptides is mediated by proteases, and is further tunable by the incorporation of specific amino acid sequences or control over their self-assembled structures. Once finishing their duty as carriers, the peptides in the peptide-based supramolecular nanofiber hydrogels of the present invention will serve as nutrients to cells.

Applications

The molecular basis of BE-associated neoplastic progression (BEAN) has been studied, with altered miR expression found to be heavily involved in this process. To the best of the inventors' knowledge, no attempts have been made to apply these molecular abnormalities to the development of therapeutic strategies and that the inventors are the first to do so in the embodiments of the present invention. Extracellular vehicles (EVs) have also been researched, but to the best of the inventors' knowledge no one has attempted to use EVs as therapeutic agents in the treatment or prevention of BEAN and the inventors' are the first to do so in the embodiments of the present invention. The inventors believe they were the first to discover EVs have the ability to carry therapeutic miRs to BEAN and may be used as miR delivery vehicles to treat or prevent disease such as cancer as an example, and more specifically EAC. The inventors determined EVs present several advantages as carriers of therapeutic miRs to BEAN. First, like miRs, they are natural structures that exist physiologically in the human body. This characteristic stands in stark contrast to most drugs and delivery vehicles such as nanoparticles, which represent foreign substances. Second, EVs are small, making it easy for them to pass through microcellular structures and cell membranes: this trait contrasts with antibodies, which are much larger and encounter barriers in these settings. Third, EVs hold the promise of no immunogenicity (in contrast to virtually any other synthetic delivery vehicle). EVs used in the present invention can be synthetized from patient's own fibroblasts cultured in vitro. To best of Inventors' knowledge, there have been no publications describing the use of BE organoids, or EVs, as models to design BEAN-preventive interventions. The inventors have designed unique protocols that make BE organoid culture much easier. This inventor's technique is quite fortunate, since organoids present several advantages over monolayer cell lines. First, BE cell lines are less physiologic, with all available lines having been obtained by immortalization using telomerase and such immortal cell lines differ dramatically from primary BE epithelia both biologically and at the molecular level. Second, BE cells are two-dimensional, again not reflecting the physiologic BE setting in vivo as well as the three-dimensional organoids. Third, BE organoids have functional features that can be monitored as indicators of neoplastic progression, such as electrolyte transport and acidic mucin secretion. Finally, although tethered sponges have been evaluated as retrieval devices for esophageal biomarker assays, no one has yet considered their development as a delivery mechanism.

Animal Model Strategy

The inventors chose to test the present invention in pigs, due to the marked anatomic similarity between human and porcine luminal GI tracts, as well as the years of expertise the inventors have using pigs for other experimental applications. The inventors plan to endoscope pigs while the Therasponge© is in place, verifying both its expansion in the stomach and its compression in the distal esophagus; the esophagus will be sampled both prior to sponge expansion and after sponge compression, providing an ideal control-experimental comparison within an almost identical time window, minimizing any variability in miR levels due to nonspecific physiologic disturbances more likely to occur between remote timepoints. The inventors plan to analyze and compare both EV levels and miR levels in the pre-EV treatment control biopsies vs. the post-treatment experimental biopsies.

Selection of the Best Therapeutic miRs Based on BE-EAC Step-Wise Field Defect Data The inventor studies have identified differentially expressed miRs in fields of BE that contained HGD or EAC. Several miRs were identified whose expression was upregulated in BE vs. NE and remained even more markedly upregulated in EAC. E.g., the miR-25-106b polycistron followed this expression pattern (data not shown). MiR-25 was 2.27-fold higher in BE than in NE, and 9.16-fold higher in EAC than in NE (i.e., 4.03-fold higher in EAC than in BE). This trend held not only in matched samples from the same patients, but also for means of all BE and EAC tissues studied. Moreover, oncogenic properties were observed both in vitro and in vivo for miRs-25, -93, and -106b: viz., inhibitors of these miRs reduced cell proliferation, while mimics increased it; inhibitors also significantly repressed nude mouse xenografted tumor growth. Finally, these miRs were found to act by silencing the potent tumor suppressor genes (TSGs) p21 (for miRs-93 and -106b) and B-cell lymphoma 2 (BCL2)-L11, also known as Bim (for miR-25). Analogous findings were also observed for downregulated miRs: e.g., miR-138 was 4.3-fold lower in BE than in NE and 500-fold lower in EAC than in NE (i.e., 139-fold lower in EAC than in BE). Again, this trend held for matched patient samples as well as for the groups as a whole.

Fibroblasts Transfer miRs Via EVs to Cancer Cells In Vitro

Figure 2:
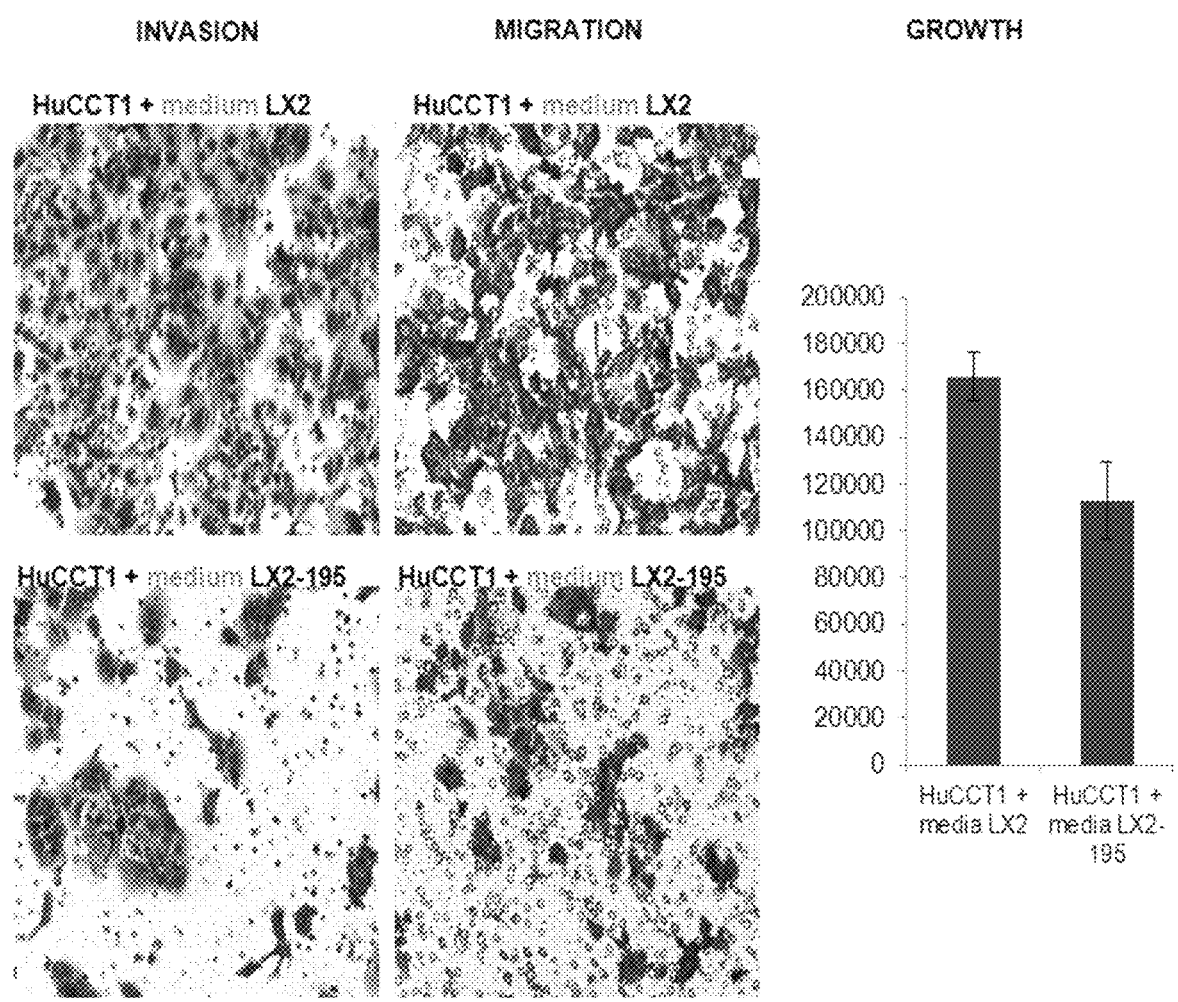
FIG. 2 illustrates upregulation of miR-195 in fibroblasts inhibits co-cultured cancer cells that are permitted to exchange media, but are not in direct contact with fibroblasts. From left to right, these panels demonstrate decreased invasion, migration and growth, respectively, of cancer cells induced by mediators released into media by LX2-195 cells vs. LX2-control cells.

The inventors generated data in a parallel model system (cholangiocarcinoma) showing that EVs are taken up by human biliary cancer cells and by cancer-associated fibroblasts (CAFs), and in fact that these EVs can transfer miRs from one cell type to the other. Furthermore, the inventors have generated data showing that miRs loaded by us into EVs can silence target mRNAs in the target cells, and exert therapeutic, anti-carcinogenic effects, both in vitro and in vivo. The inventors identified a miR species (miR-195) as down regulated in this cancer. Next, based on the methods of the present invention, the inventors loaded miR-195 into EVs. These EVs were then administered to cancer cells in vitro. Cancer cells uptook EVs and utilized their cargo (miR-195) in their cytoplasm followed by inhibition in their growth and invasion. Last, EVs loaded with miR-195 were given intravenously to rats bearing cancer in their livers. EVs were then demonstrated in the cancer mass. The cancer regressed, and survival increased. Furthermore, the inventors found that the EV nucleic acid cargo was utilized by cancer cells. Specifically, cancer cells exposed to miR-containing therapeutic EVs displayed significant reductions in invasion, migration, and growth vs. control cancer cells (FIG. 2).

Figure 3:
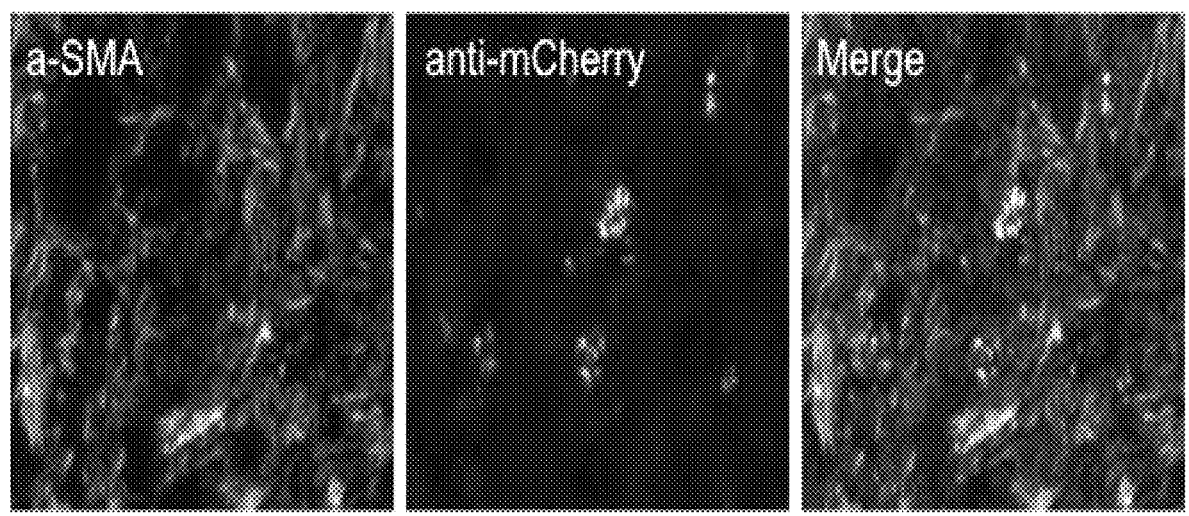
FIG. 3 illustrates fibroblast-derived EVs are selectively targeted to cancer cells in vivo. Rats with CCA tumors were injected with fibroblast-derived EVs containing the TSG101/mCherry protein. 2 days later, animals were sacrificed and areas of tumor stained with (left panel) fluorescent antibodies to alpha-SMA, which stains activated fibroblasts, and (middle panel) FITC-conjugated antibodies to the mCherry portion of the vesicle-enclosed TSG101/mCherry marker protein. Note that the injected vesicles are selectively enriched in pockets of tumor that contained primarily cancer cells.
Figure 4:
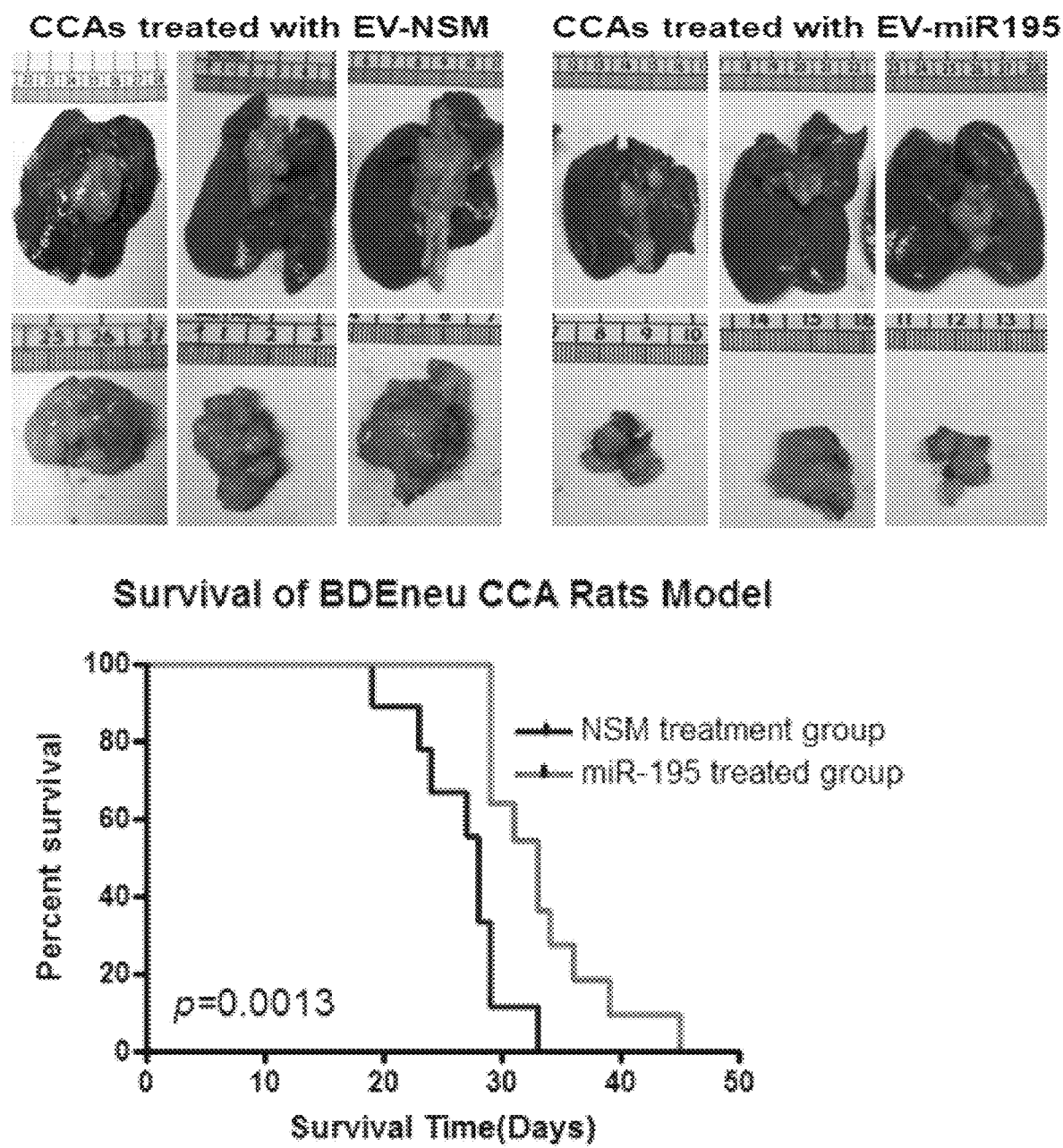
FIG. 4 illustrates MiR-195-loaded EVs inhibit CCA growth and increase survival In vivo. Fibroblast-derived EVs were loaded with either a non-specific miR mimic (left panels) or a miR-195 mimic (middle panels) and injected into rats with CCA. 30 days later, rats were sacrificed. Examination of entire liver (left upper panels) and excised tumor (left lower panels) revealed that tumors were significantly smaller in animals that had been injected with miR-195-loaded EVs. Twenty cancer bearing rats were divided into 2 groups: 11 were treated with EVs-miR-195 and 9 were treated with EVs-NSM (negative control). In vivo treatment of CCA with EVs-miR-195 increased survival by 50%.

Fibroblast-Derived Extracellular Vesicles (EVs) are Selectively Targeted to Tumor Cells In Vivo The possibility that EVs might contribute to the CAF-to-cancer signaling observed above led the inventors to ask whether fibroblast-derived EVs might be targeted to tumor cells in vivo. To address this possibility the inventors generated LX2 cells that constitutively express an EV marker protein, a TSG101/mCherry fusion protein (TSG101 is secreted from the cell in EVs, which allowed the inventors to selectively detect these fibroblasts-derived EVs using antibodies specific for mCherry. The resulting cell line, LX2-TSG101/mCherry, was grown for several days and the EVs that it secreted were collected from the tissue culture supernatant by standard procedures. The purified, TSG101/mCherry-labeled, fibroblast-derived EVs were then injected into the tail veins of rats, which had been injected with BDEneu tumor cells 24 days earlier and thus had already developed CCA in their livers (we have extensive experience with this model of CCA). Twenty four hours after injection, we sacrificed the rats, removed their livers, lungs, and kidneys, generated slides of these tissues, and processed them for immunofluorescence microscopy using antibodies specific for alpha-Smooth Muscle Actin (which stains activated, collagen-producing fibroblasts) and mCherry to detect fibroblast-derived, TSG101-mCherry-containing exosomes/EVs. These experiments revealed that fibroblast-derived EVs were highly enriched in "pockets" of cancer cells within the fibrotic CCA mass in the liver (FIG. 3). The inventors did not detect staining for TSG101/mCherry in non-cancerous liver, lung, or kidney. These results indicated that fibroblast-derived EVs are selectively targeted to CCA tumors and can deliver EV-associated molecules to CCA cells in vivo. Furthermore, rats with orthotopic tumor xenografts who had been treated with intravenous miR-195-containing EVs developed smaller tumors and exhibited prolonged survival (FIG. 4).

BE Organoids

Figure 5:
FIG. 5 illustrates the establishment of organoids from human BE biopsies. Freshly obtained endoscopic biopsies were processed according to protocols learned in the JHU GI Core Center after our own modifications. The organoids grew well and could be propagated for periods of ≥3 months; they were also successfully frozen down and re-cultured after thawing.

With training from the Enteroid Core Lab of the JHU GI Core Center, the inventors have acquired expertise in the establishment, propagation, manipulation, and storage of BE-derived enteroids (organoids). The inventors established and treated BE organoids with the known COX-2 inhibitor and chemopreventive agent, sulindac. The organoids grew quite well with our custom modifications of the culture medium ingredients (FIG. 5). A dose-related response in expression of the STAT3 gene, which exhibits known involvement in BEAN and is known to respond to sulindac in other systems, was detected by RT-PCR analysis of RNA extracted from treated BE organoids (data not shown).

Endoscopic Procedures in Pigs

The inventors have extensive endoscopic expertise in pigs and have performed endoscopy as well as endoscopic gastrointestinal interventions in more than 200 pigs. The inventors' experiments included diagnostic endoscopy, endoscopy-assisted induction of rectal inflammation, endoscopy-assisted delivery of minirobots (microgrippers), as well as performing of advanced procedures, such as Endoscopic Retrograde Cholangio Pancreatography (ERCP). The porcine gastrointestinal tract bears a striking similarity to humans', making this model eminently feasible and desirable. The most notable difference is the presence of a Zenker's diverticulum in the vast majority of pigs, which only poses a challenge to inexperienced endoscopists. Trained personnel anesthetize pigs and place intravenous catheters for blood draws as well as intravenous anesthetic administration. Pigs are continually monitored for cardiovascular or respiratory complications. The endoscopic equipment is the same as utilized in humans, including endoscopes, endoscopic tools, therapeutic substances and image analysis software.

EsophaCap Sponge Device

Figure 6:
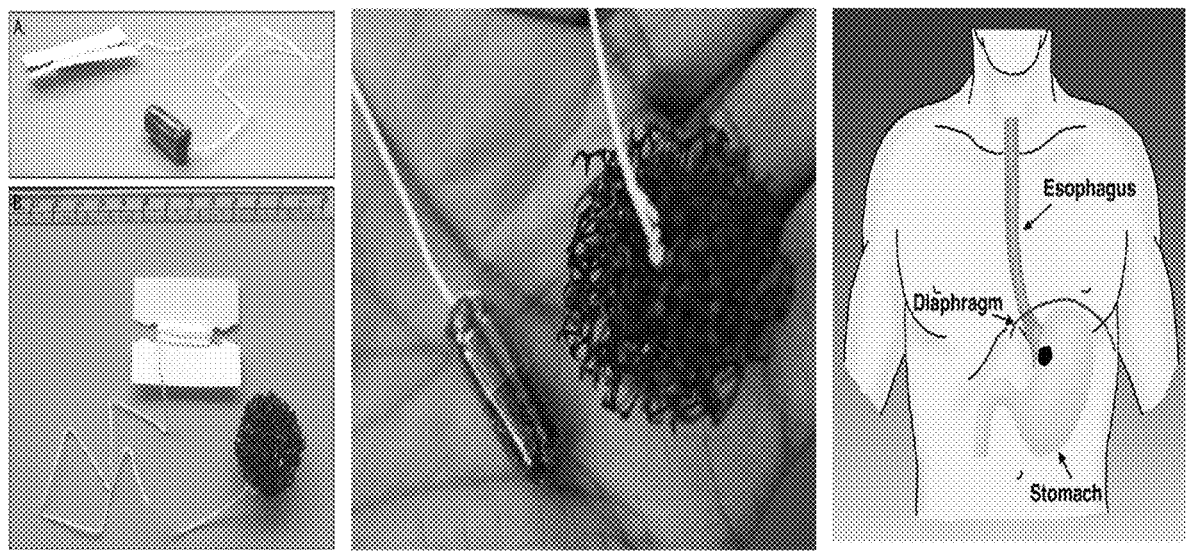
FIG. 6. CapNostics EsophaCap™ Swallowable FDA 510k-Approved Sponge. The collapsible black plastic sponge is tethered to a filament and compressed within a soluble gelatin capsule. The end of the filament is held outside the mouth while the capsule is swallowed. Once inside the stomach, the capsule dissolves after several minutes and the sponge expands. It is then retrieved by pulling on the filament. In classical use, cytologic material attaches to the sponge during exit, including cells from EAC or HGD, as well as from surrounding BE (if present) and normal esophagus (NE). In the current application, the sponge will be impregnated with a supramolecular hydrogel containing EVs loaded with one or more therapeutic microRNAs (miRs).

In collaboration with Dr. Martin von Dyck of Capnostics, LLC (Upper Black Eddy, Pa.; see letter), we have obtained and tested an encapsulated tethered sponge (EsophaCap: FIG. 6).

EVs in Supramolecular Hydrogel for miR Delivery to Esophageal Epithelial Cells

The present invention provides a convenient method to deliver EVs to the esophagus for successful local prevention of BEAN. Upper gastrointestinal (GI) endoscopy could guide the delivery of EVs with high precision but is inconvenient and costly. As a matter of fact, BE patients currently have no non-invasive, point-of-care therapeutic options. The present invention including a swallowable tethered sponge offers an alternative strategy to address the above-mentioned issue, the success of which depends on the realization of three key technical challenges: first, how can the EVs be loaded into the sponge with controllable and accurate dosage; second, how can the EVs be released efficiently from the sponge during its passage through esophagus; and third, how can the EVs be retained on the surface of the esophagus for a prolonged period of time. Given that the EVs are hydrophilic in nature and need to transfer their cargo from the sponge to the esophagus within only a few minutes, hydrophobic materials and covalent immobilization of EV to the sponge should be avoided. Direct adsorption of EVs to the surface of sponge would require sophisticated modification of the sponge surfaces. Nanoparticle-hydrogel composite is an emerging platform technique to immobilize medicines for local drug delivery, taking advantage of superior properties of both nanomedicine (e.g., protection, targeting) and hydrogels (e.g., immobilization, controlled release). However, conventional hydrogels are made of covalently cross-linked polymers, and thus the release of trapped cargos is dependent upon polymer chain degradation, which could retard the efficient release of EVs required for the proposed application. In addition, the high viscosity of high-molecular weight polymers may lead to difficulties in capsule loading. Suitable hydrogels of the present invention include self-assembling supramolecular hydrogels having ideal properties for impregnating gelatin capsules with an EV-containing sponge, and for facilitating effective release of EV to the esophagus walls.

Design, Synthesis, Characterization and Evaluation of Supramolecular Nanofiber Hydrogels Using Small Molecule Peptides.

Figures 7A, 7B, 7C, 7D:
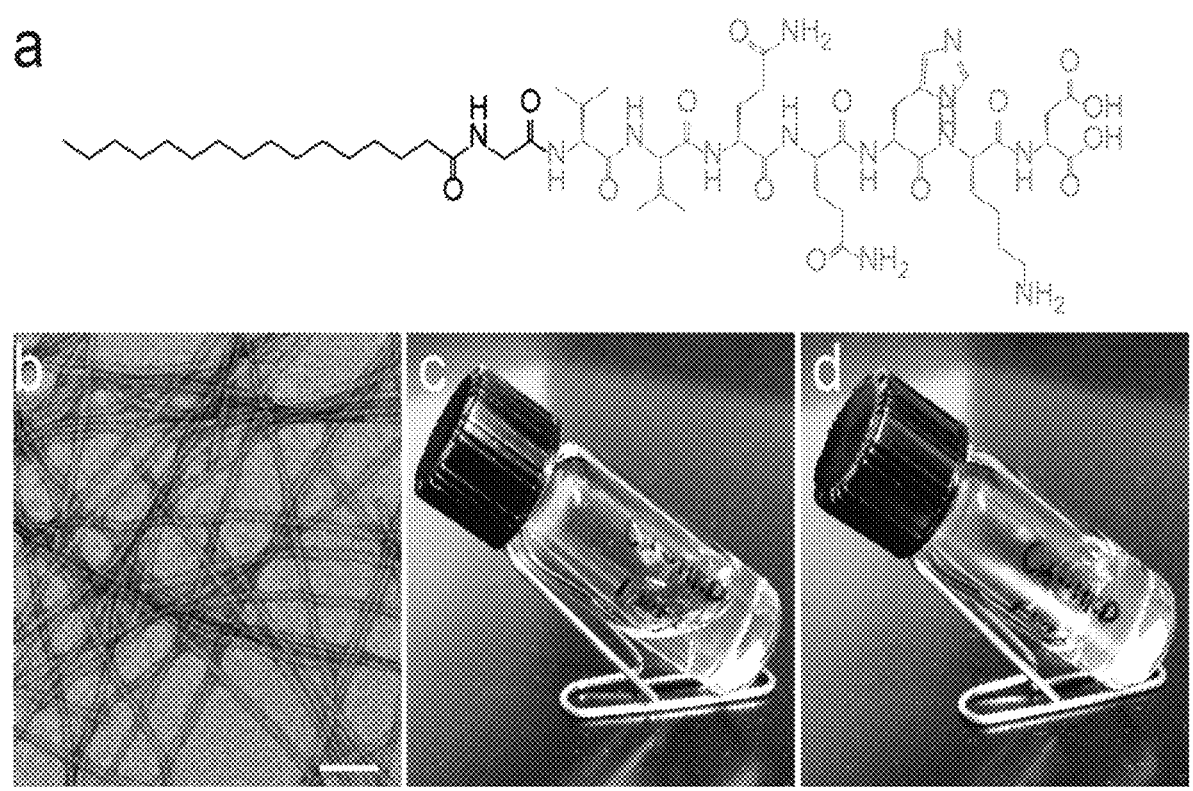
FIG. 7A-7D. Sol-gel transition of $C_{16}$-HKD solution. (a) Molecular structure of $C_{16}$-HKD. (b) Nanofibers formed by the self-assembly of monomers. The solution was liquid shortly after dissolution (c), but turned into self-support hydrogel after prolonged incubation (d). Scale bar: 100 nm.

The inventors identified, a leading molecule, $C_{16}$-HKD peptide amphiphile (PA), found to realize the desired sol-gel transition (FIG. 7). In a typical design, PAs have 3 key structural features, illustrated by the molecular structure of $C_{16}$-HKD (FIG. 7a). Region 1, the hydrophobic domain, consists of a long alkyl tail or any other hydrophobic units, depending on the purpose of the application. Region 2 comprises hydrophobic amino acids with a strong propensity to form intermolecular hydrogen bonds, typically in the form of β-sheets. This unique feature leads to the 1D nature of the resulting self-assembled nanostructures. Region 3 contains charged amino acids for enhanced solubility in water and for the design of pH and salt responsive nanostructures and networks. The $C_{16}$-HKD assembled into short nanofibers shortly after dissolution, but eventually turned into self-supporting hydrogel due to supramolecular growth and entanglement of the nanofibers.

Embodiments of the disclosure concern methods and/or compositions for treating and/or preventing BE-associated neoplastic evolution (BEAN) and/or esophageal adenocarcinoma in which modulation of one or more EAC pathway or of one or more tumor suppressor gene in cancer or pre-cancer cells is directly or indirectly related. In certain embodiments, individuals with cancer or pre-cancer such as BEAN and or esophageal adenocarcinoma are treated with one or more miRs preferably using a device of the present invention.

In certain embodiments, the level to which one or more miRs of the present invention suppresses one or more EAC pathways or silences one or more tumor suppressor genes in cancer or pre-cancer cells may be any level so long as it provides amelioration of at least one symptom of the esophageal disorder, including BEAN or EAC. The level of suppression of one or more EAC pathways or the silencing of one or more tumor suppressor genes in cancer or pre-cancer cells may decrease by at least 2, 3, 4, 5, 10, 25, 50, 100, 1000, or more fold expression compared to the level of expression in a standard, in at least some cases. An individual may monitor expression of the EAC pathways or of the tumor suppressor genes in cancer cells using standard methods in the art, such as northern assays or quantitative PCR, for example.

An individual known to have BEAN or EAC, suspected of having BEAN or EAC, or at risk for having BEAN or EAC may be provided an effective amount of a modulator of one or more EAC pathways or of one or more tumor suppressor genes in cancer or pre-cancer cells, including one or more miRs of the present invention. Those at risk for BEAN or EAC may be those individuals having one or more genetic factors, may be of advancing age, and/or may have a family history, for example.

In particular embodiments of the disclosure, an individual is given an agent for BEAN or EAC therapy in addition to one or more miRs of the present invention that modulate one or more EAC pathways and/or one or more tumor suppressor genes. When combination therapy is employed with one or more miRs of the present invention, the additional therapy may be given prior to, at the same time as, and/or subsequent to the miRs of the present invention.

Certain methods of the disclosure provide for methods of diagnosing BEAN or EAC prior to the therapeutic methods of the disclosure, and such diagnosis may occur by any methods or means, including at least genetic marker assay, single-photon emission computed tomography, olfactory system testing, autonomic system testing, or a combination thereof.

Pharmaceutical Preparations

Pharmaceutical compositions of the present invention comprise an effective amount of a modulator of an EAC pathway and/or a tumor suppressor gene, such as one or more miRs of the present invention, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one miRi of the present invention or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The modulator of one or more EAC pathways and/or one or more tumor suppressor gene, such as one or more miRs of the present invention, may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The miRs of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include the miRs of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the miRs of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the miRs of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, inducer of expression of PGC-1 may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound or the miRs of the present invention may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, an modulator of one or more EAC pathway and/or one or more tumor suppressor gene (for example, one or more miRs of the present invention) may be comprised in a kit. The kit may also comprise EVs, hydrogels, and sponges of the present invention.

The kits may comprise a suitably aliquoted miRs of the present invention and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the miRs of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The miRs may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Selection of the Best Therapeutic miRs

The inventors will select 6 therapeutic ts-miRs (miRs with sequentially decreasing expression during progression from BE to dysplasia to frank cancer) based on the inventors own BE-EAC field defect miR expression data. The inventors will first validate miRs they have selected based on a comprehensive survey of the literature showing tumor-suppressive effects of these miRsin vitro and/or in vivo. MiRs that have not demonstrated strong anti-oncogenic properties in cells, animals, or other model systems, even miRs with marked and consistent fold-changes between NE and both BE and EAC, will be discarded. The inventors plan to leverage all published miR literature in esophageal cancer, including the inventors' preliminary and published work, with the purpose of elevating these knowledge to a therapeutic, immediately useful, product. Examples of miRs used in the methods of the present invention include:

hsa-mir-106b MI0000734

(SEQ ID NO: 1)
CCUGCCGGGGCUAAAGUGCUGACAGUGCAGAUAGUGGUCCUCUCCGUGC
UACCGCACUGUGGGUACUUGCUGCUCCAGCAGG

-continued

Has-mir-93 MI0000095

(SEQ ID NO: 2)
CUGGGGGCUCCAAAGUGCUGUUCGUGCAGGUAGUGUGAUUACCCAACCU
ACUGCUGAGCUAGCACUUCCCGAGCCCCGG hsa-mir-25 MI0000082

(SEQ ID NO: 3)
GGCCAGUGUUGAGAGGCGGAGACUUGGGCAAUUGCUGGACGCUGCCCUG
GGCAUUGCACUUGUCUCGGUCUGACAGUGCCGGCC

Experimental Design

The experimental flow of the present invention will be as follows: a) The inventors' miR microarray and RT-PCR data will be analyzed to select the 6miRs most markedly and consistently downregulated between BE and EAC. A further selection criterion will include data showing tumor-suppressive activity in vitro and/or in vivo for the selected miRs in esophageal cells and/or other organs. Such data, is believed by the inventors, constitute evidence of potential cancer-preventive effectiveness (for ts-miRs, miR-mimics will constitute appropriate therapeutic agents).

Methods

MiR microarray data will be prioritized by significance analysis of microarray data (SAM), which creates a score based on both average fold-change between groups and the significance of those differences by t-testing. The first filtering step will be to select the top 50 miRs based on SAM score for both EAC vs. BE and BE vs. NE. For the next filtering step, miRs exhibiting the most marked sequential down-regulation at all 3 serial progression levels will be chosen (i.e., where EAC/NE>EAC/BE and EAC/NE»BE/NE). Thus, miRs will be ordered according to serial EAC/BE/NE ratios: the top 10 miRs in this ordering will be selected for use in the present invention. The final filtering step, comprehensive literature searches (as well as searches of the inventors' previous data) will be conducted to assess evidence of in vitro or in vivo miR tumor-suppressive activity, with in vivo activity given higher priority, and effectiveness in esophageal cells or animal models given higher priority than effectiveness in cells or models derived from other organs. After filtering has been completed, the candidate miRs will be overexpressed in 3 EAC cell lines by transfection. The inventors will then describe phenotypically the effects on growth and invasion. Only miR species that the inventors can verify in their laboratory to exhibit cancer-inhibiting effects will be selected.

Methods to Deliver EV-Carried miRs to Esophageal Epithelial Cells In Vitro

The present invention demonstrates that the inventors' delivery of miRs by EVs obtained in a system such as liver cancer occurs in EAC cells and BE organoids.

Experimental Design

The present invention will use the following experimental flow: 2a) EVs will be manipulated to express high levels of therapeutic miRs. Next, EVs containing mimics of serially downregulated miRs will be applied to BE cell lines. Uptake of vesicles will be verified by labeled EV imaging. Transfer of miRs will be verified by pre vs. post-application RT-PCR; 2b) EVs containing these miRs will be applied to BE organoids. Uptake will be assessed as in 2a; 2c) BE cell lines and organoids will be assessed for phenotypic effects of transferred miRs: i) By measuring levels of known mRNA targets of these miRs; ii) By assessing growth rate, apoptosis, migration/invasion, morphology, and cell cycle progression.

Cell Lines

For these experiments, the inventors will use the EAC-derived cell lines JHU-Ad1, OE33, Flo-1, and SKGT4. All of these cell lines are already actively growing in the inventors' laboratory, and the inventors have used them in previous published experiments.

Organoids

The inventors are actively culturing organoids from endoscopic BE biopsies. This procedure will be continued as described, but with modifications of culture conditions instituted in the inventors' laboratory, chiefly the addition of certain important additional growth factors.

EV Transfection with miR-Mimics

The inventors will isolate EVs from cells and organoids grown in exosome-free culture medium, as described previously by the inventors. Next, the inventors will measure exosome content by measuring the protein content in the suspended exosomes (based on a BCA protocol). The inventors will then transfect EVs through a modified lipofectamine protocol, followed by re-isolation of EVs.

Retroviral/Lentiviral Constructs

Figure 8:
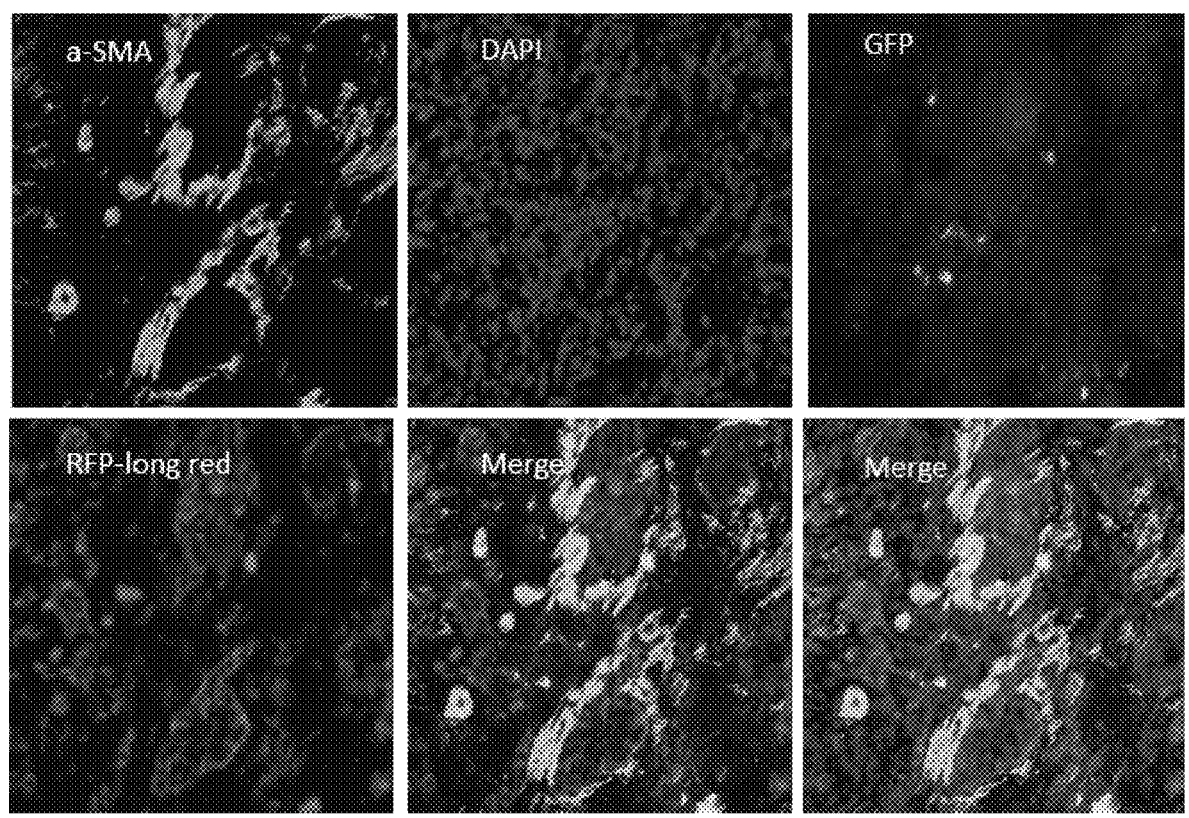
FIG. 8. BDENeu cells were infected with a viral construct loxpP-dsRed-loxp-eGFP. Next, cells selected for the consistent expression of the construct, were injected in the liver of rats in vivo. After the tumors grew, we delivered EVs containing Crevia tail vein. Rats were euthanized, and the following antibodies were applied to slides: alpha-SMA (to stain for fibroblasts), DAPI (nuclear stain), anti-EGFP antibody (to reveal cancer cells that switched color due to taking up EVs loaded with Cre), anti-RFP (to reveal cancer cells that did not take upCre). Shown is the typical and expected appearance of intrahepatic cholangiocarcinoma, with cords of fibroblasts (stained with anti-alpha SMA antibody), as well as pockets of cancer cells (most of which are red in the Figure). Also note cells that switched color from red to green. Note that these cells lie within pockets of cancer cells. Note that there is no green staining of fibroblast cords.

As provided in the inventors' published manuscripts, for each miR of choice, the inventors will clone the genomic sequence into MIEG3, infect cells or organoids, then sort for GFP positivity. The inventors will also utilize lentiviral constructs expressing TSG101/mCherry selectable by puromycin. Cells infected with these constructs and selected by the antibiotic resistance gene will make mCherry-positive (red) extracellular vesicles. The inventors will then utilize anti-mCherry antibodies to identify the EVs in vitro as well as in vivo. Last, the inventors will utilize a Cre/LoxP-LoxP lentiviral construct. In brief, cells or organoids will be infected with a lentiviral construct that transduces the following sequence—loxP-dsRed-loxP-eGFP. Next, the inventors will transfect Cre DNA into EVs, as they have done in previous experiments (FIG. 8). Cells or organoids not exposed to EVs carrying Cre will demonstrate red fluorescence, while those exposed to EVs carrying Cre, which also utilized Cre in their cytoplasm, will demonstrate green fluorescence. The inventors have utilized this system both in vitro and in vivo, as shown in FIG. 8.

Flow Cytometric Determination of GFP

A donor cell line (SKGT4 EAC cells, designated "DEAC") will be utilized to produce EVs. A recipient cell line (FLO-1 EAC cells, designated "REAC") will be utilized to test how the EVs from the donor line are taken up and the cargo utilized. For transfection experiments, the REAC cells will be transfected to make them GFP-positive, while the DEAC cells will be non-fluorescent. For viral transduction experiments, DEAC cells will be transfected to make them GFP-positive and REAC cells will be non-fluorescent. The inventors will employ a FACS Aria sorter.

Cell Cycle Analysis by Flow Cytometry

Flow cytometric analysis of DNA content will be performed to assess cell cycle phase distribution. After sorting, cells will be stained with propidium iodide (PI). DNA content will be evaluated using the same FACS Calibur flow cytometer (BD Biosciences, San Jose, Calif.) and CellQuest software (BD Biosciences) for histogram analysis.

Apoptosis Assays with Annexin V and PI

After sorting, cells or organoids (disaggregated by digestion with collagenase) will be washed twice with ice-cold PBS and then treated for 20 minutes, at room temperature, with 5 uL of Annexin V and 5 uL of PI. Cells or organoids will then be analyzed for Annexin V/PI staining within one hour on a FACS Calibur cytometer (BD Biosciences, San Jose, Calif.).

Scratch Assays

This assay will be performed as previously described.
Cell migration and invasion assays.
Cell Migration and Invasion Assays The inventors will employ Transwell and Matrigel chamber plates (24-well-format, BD Biosciences), as described.

A Delivery System Comprising a Retrievable Sponge-Like Device Impregnated with Hydrogels Containing miR-EVs The inventors have demonstrated that EVs administered intravenously concentrate in the tumor mass, decrease the size of the tumor mass and induce increased survival and in the present invention will deliver EVs locally for better topical concentration and less potential system side effects.
Experimental Design The present invention will use the following experimental flow: 3a) the inventors will first modify the EsophaCap sponge by adding supramolecular gels containing miR-containing labeled EVs to it; 3b) the inventors will next administer this modified sponge to pigs endoscopically; 3c) the inventors will then verify the transfer of labeled EVs to porcine mucosa by esophageal biopsy; and 3d) the inventors will verify transfer of miRs and suppression of their target mRNAs by mucosal biopsy.
Develop the EsophaCap Sponge into the Therasponge.

Figure 9:
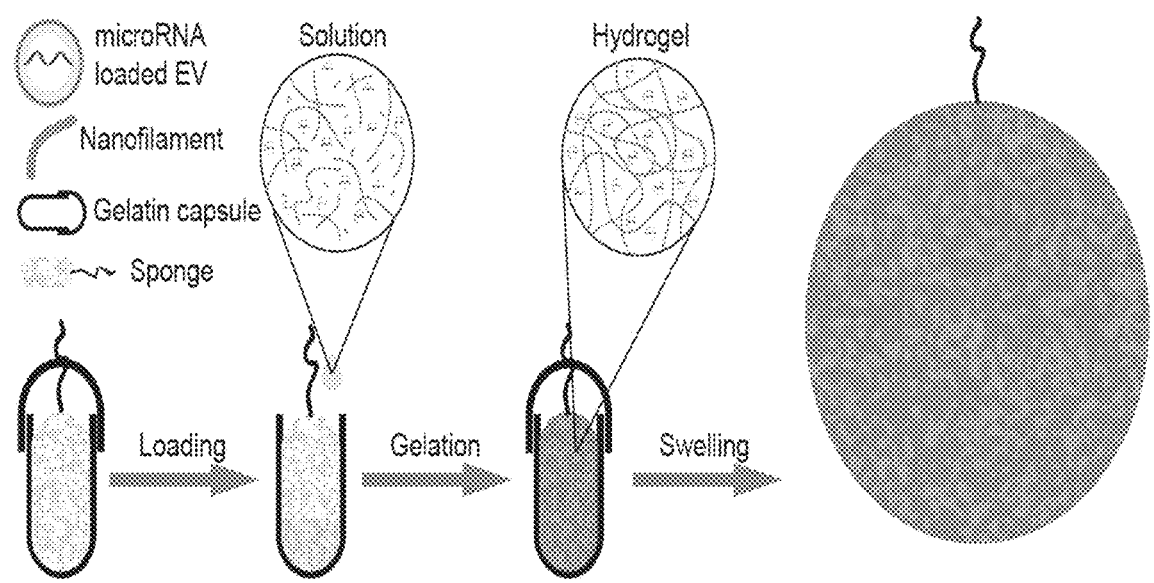
FIG. 9. Schematic illustration of loading EVs into sponge impregnated with supramolecular hydrogels. The sponge in the capsule is loaded with a solution mixture of miR-loaded EVs and short nanofibers that are formed by self-assembly of relationally designed peptide amphiphiles. With incubation, the nanofiber solution gradually turns into a gelation state as a result of the elongation and entanglement of the nanofibers. The gelatin capsule will dissolve in the stomach, thus leading to the expansion of the sponge, which is filled with the peptide nanofiber hydrogel with homogeneously dispersed EVs.

The hydrogel-assisted procedure of loading EVs into the gelatin capsule is illustrated in FIG. 9. The inventors believe that the EVs of the present invention can be homogeneously dispersed in the solution of a mixture of unassembled peptide amphiphile monomers and short nanofibers, which can easily fill the gelatin capsule containing the sponge due to its low viscosity. Gelation will take place with time as a result of nanofiber growth, or be triggered by temperature to immobilize the EVs within the hydrogel. The nanofiber hydrogels will expand with the sponge upon gelatin dissolution in stomach, and may swell slightly but will not dissolve. During their travel into the distal esophagus, the shear thinning properties of these hydrogels will allow for smooth and gradual transfer of EV-containing hydrogels onto the esophageal walls. The high viscosity offers strong adhesion to the esophagus and prolonged EV exposure, and thus efficient miR delivery.

To achieve optimal EV delivery, the molecular design of the present invention requires further optimization according to our results obtained from $C_{16}$-HKD hydrogels (see above). For the optimized hydrogel, the inventors believe that: first, the designed materials will not disrupt the EVs; second, the hydrogel will be reasonably stable in acidic fluid presented in the stomach; third, the hydrogel will be rigid enough to withstand shear and not break up during its traverse through the esophagus; and fourth, the hydrogel will adhere to epithelial cells of the esophagus, allowing efficient transfer of the encapsulated cargo.

The present invention has optimized the inventors' PA molecular design by varying both the hydrophobic segment, the middle β-sheet forming region, and the terminal hydrophilic residues. Peptide amphiphiles that have low exchange rates with insertion into EVs should be selected. For hydrophobic block, hydrocarbons of varying lengths will be tested to tune the assembly and gelation behavior. For hydrophilic block, the inventors will tune their sequence based on the preliminary result collected from $C_{16}$-HKD to make it easier to form hydrogel by replacing valine or glutamine with phenylanine or tyrosine. The terminal group of hydrophilic peptide will also be tested, and neutral of negatively charged hydrophilic sequence will be preferred since positive charge could disrupt the vesicles through strong electrostatic interaction. The chemical stability of the amphiphiles will be tuned by the use of D-amino acids in the peptide sequence design. The terminal group of the amphiphiles will also be explored for suitable pH responsibility, hydrophilicity and bioactivity. After the molecular design has been optimized, the concentration of the monomers will be explored to achieve balanced rigidity and viscosity. As an alternative approach, co-assembly of the amphiphiles of the present invention with biopolymers such as hyaluronic acid will be explored to tune the viscosity and rigidity.

Refine the Therasponge In Vivo in Porcine Models

Endoscopy (EGD).

After anesthesia and while monitoring pig vital signs, an EsophaCap sponge will first be inserted transorally and advanced the proper distance to place it in the stomach (judged by distance markings on the sponge tether). Next, a standard upper endoscope (GIF-160, Olympus) will be advanced into the stomach, alongside the EsophaCap tether. During initial insertion of the endoscope, two control (pre-EV treatment) biopsies will be obtained from the distal esophagus. The location of the sponge will be verified (by direct EGD visualization) as in the stomach. If the sponge is not in the stomach, it will be advanced or withdrawn under direct endoscopic guidance until it is in the stomach. The sponge will be permitted to remain next to gastric mucosa, within the minimal gastric fluid present. It will be observed until its gelatin capsule dissolves (from human experience with similar sponge devices, this should take approximately 3-5 min). After the capsule dissolves and the sponge fully expands, it will be withdrawn under direct endoscopic guidance via the tether into the distal esophagus (viz., within the lower esophageal sphincter or at the GE junction), with the endoscope being pulled back into the esophagus in parallel. The sponge will then be observed and verified to be compressed by the pig's esophageal peristaltic contractions. It will be left in place for 5 min, after which it will be advanced into the stomach again. At this point, the esophagus will be washed endoscopically to remove EVs from the mucosal surface, after which 2 post-EV treatment biopsies will be taken from the distal esophagus (viz., the LES or GEJ).
Biopsy Processing and EV/miR Assays Biopsies will be placed in PBS at room temperature and transported to the inventors' laboratory, where EV imaging (via labeling transferred EVs) and miR levels (via qRT-PCR), as well as measurement of miR target mRNA levels (also via qRT-PCR), will be performed in both control and experimental biopsies, as described.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

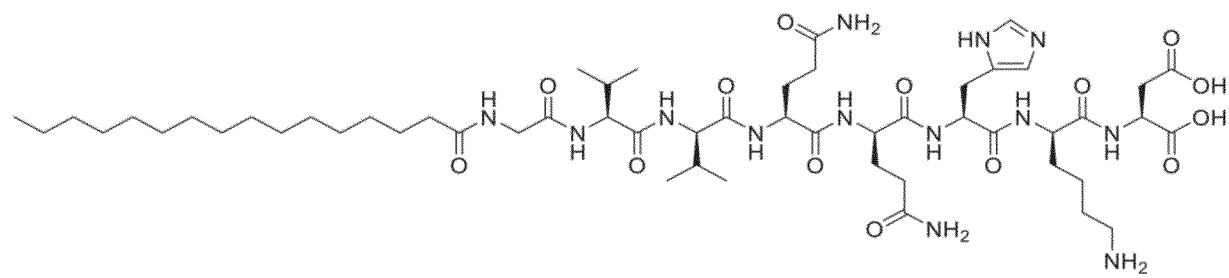

The invention claimed is:

1. A device for transferring an agent to esophageal cells in a subject having a disease selected from Barrett's esophagus, low-grade dysplasia, high grade dysplasia, esophageal adenocarcinoma, and a combination thereof, said device comprising:
   a) a retrievable sponge compressed within a soluble gelatin capsule impregnated with a hydrogel c16-HKD peptide nanofiber hydrogel comprising nanofibers having the structure of formula I:

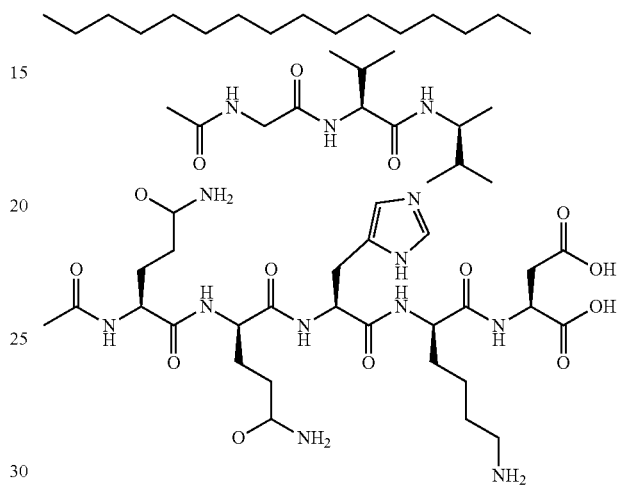

SEQUENCE LISTING

```
<160> NUMBER OF SEQ ID NOS: 3

<210> SEQ ID NO 1
<211> LENGTH: 82
<212> TYPE: RNA
<213> ORGANISM: Homo sapiens

<400> SEQUENCE: 1
ccugccgggg cuaaagugcu gacagugcag auaguggucc ucuccgugcu accgcacugu     60
ggguacuugc ugcuccagca gg                                             82

<210> SEQ ID NO 2
<211> LENGTH: 80
<212> TYPE: RNA
<213> ORGANISM: Homo sapiens

<400> SEQUENCE: 2 cuggggcuc caaagugcug uucgugcagg uagugugauu acccaaccua cugcugagcu      60
agcacuuccc gagcccccgg                                                80

<210> SEQ ID NO 3
<211> LENGTH: 84
<212> TYPE: RNA
<213> ORGANISM: Homo sapiens

<400> SEQUENCE: 3
ggccaguguu gagaggcgga gacuugggca auugcuggac gcugcccugg gcauugcacu     60
ugucucgguc ugacagugcc ggcc                                           84
``` b) fibroblast-derived extracellular vesicles (EVs) comprising microRNA (miR); wherein the device is capable of being swallowed by a subject and is placed in contact with the cells in the esophagus of the subject.

2. The device of claim 1, wherein the microRNA is selected from miR-25, miR-93, miR-106b, and a combination thereof.

3. The device of claim 1, wherein the sponge is tethered to a string.

4. The device of claim 3, wherein the string has distance markings.

5. The device of claim 1, wherein the capsule dissolves after being swallowed and the sponge is located on the inside of the capsule.

6. The device of claim 1, wherein the extracellular vesicles are synthesized from a subject's own fibroblasts.

7. The device of claim 6, wherein the fibroblasts are cultured in vitro.

8. The device of claim 1, wherein the subject has Barrett's esophagus (BE).

9. A method comprising the steps of:
having a subject swallow a device for transferring an agent to esophageal cells in the subject, wherein the subject has a disease selected from Barrett's esophagus, low-grade dysplasia, high grade dysplasia, esophageal adenocarcinoma, and a combination thereof, said device comprising:

a) a retrievable sponge compressed within a soluble gelatin capsule impregnated with a c16-HKD peptide nanofiber hydrogel comprising nanofibers having the structure of formula I:

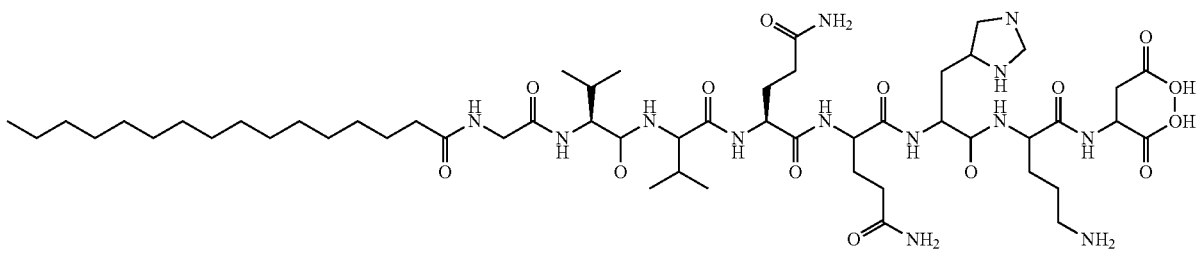 [SMILES: CCCCCCCCCCCCCCCC(=O)NCC(=O)N[C@@H](C(C)C)C(O)NC(C(=O)N[C@@H](CCC(N)=O)C(=O)NC(CCC(N)=O)C(=O)NC(CC1CNCN1)C(O)NC(CCCN)C(=O)NC1CC(=O)OOC1=O)C(C)C]

b) fibroblast-derived extracellular vesicles (EVs) comprising microRNA (miR); and wherein the device is placed in contact with diseased cells in the esophagus of the subject and transfers the miR from the device to the diseased cells.

10. The method of claim 9, wherein the subject is human.

11. The method of claim 9, wherein the subject may perform the method independently.

12. The method of claim 9, wherein the sponge is squeezed by the lower esophageal sphincter releasing the extracellular vesicles.

13. The method of claim 9, wherein the extracellular vesicles are labelled.

14. The device of claim 1, wherein the cells are diseased cells.

* * * * *

UNITED STATES PATENT AND TRADEMARK OFFICE
CERTIFICATE OF CORRECTION

PATENT NO. : 11,149,275 B2
APPLICATION NO. : 15/727653
DATED : October 19, 2021
INVENTOR(S) : Florin M. Selaru et al.

It is certified that error appears in the above-identified patent and that said Letters Patent is hereby corrected as shown below:

In the Claims

Column 26, Claim 1, Line 13 reads:

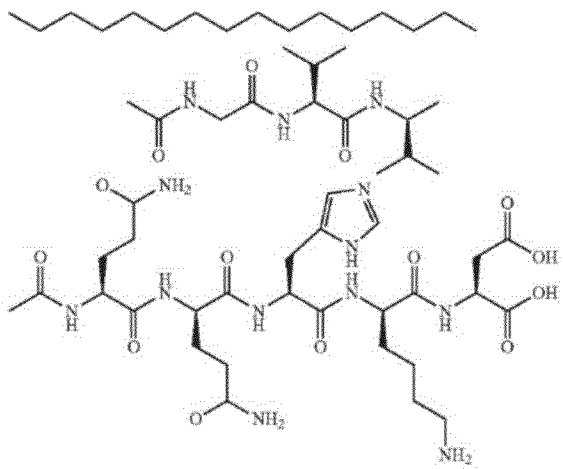

Whereas it should read:

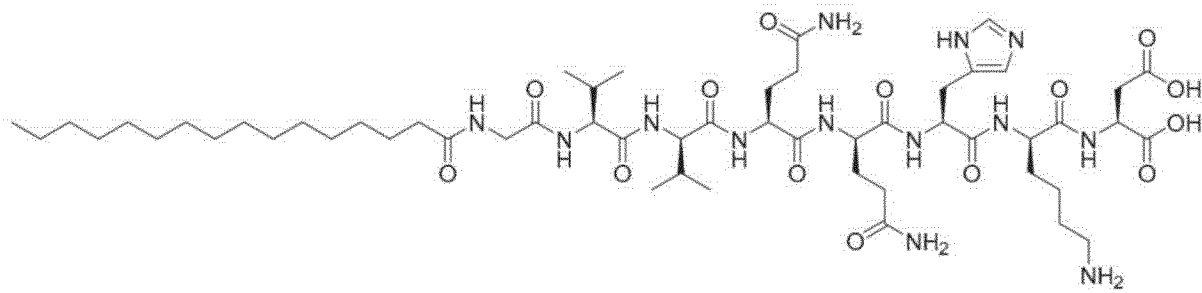

Signed and Sealed this
Eighth Day of February, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,149,275 B2

Column 28, Claim 9, Line 17 reads:

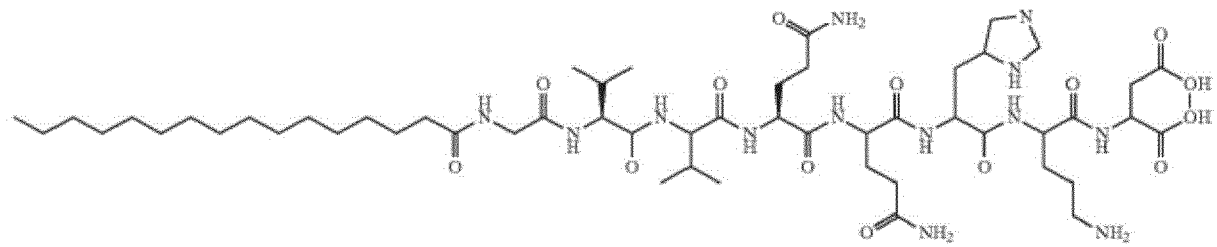

Whereas it should read: